US007410954B2

(12) United States Patent
Davidson et al.

(10) Patent No.: US 7,410,954 B2
(45) Date of Patent: Aug. 12, 2008

(54) ADENOVIRUS SEROTYPE 30 (AD30)

(75) Inventors: Beverly L. Davidson, North Liberty, IA (US); Lane K. Law, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 614 days.

(21) Appl. No.: 10/621,006

(22) Filed: Jul. 15, 2003

(65) Prior Publication Data

US 2004/0038924 A1   Feb. 26, 2004

Related U.S. Application Data

(62) Division of application No. 09/758,008, filed on Jan. 9, 2001, now Pat. No. 6,635,466.

(51) Int. Cl.
*A01N 43/04* (2006.01)
*A01N 63/00* (2006.01)
*A61K 39/00* (2006.01)
*A61K 39/295* (2006.01)
*A61K 39/235* (2006.01)
*A61K 39/175* (2006.01)

(52) U.S. Cl. .................. 514/44; 424/93.2; 424/192.1; 424/201.1; 424/233.1

(58) Field of Classification Search .................. None
See application file for complete search history.

(56) References Cited

U.S. PATENT DOCUMENTS

| 5,543,328 | A | 8/1996 | McClelland et al. |
|---|---|---|---|
| 5,547,932 | A | 8/1996 | Curiel et al. |
| 6,635,466 | B2 | 10/2003 | Davidson et al. |
| 6,998,263 | B2 * | 2/2006 | Kovesdi et al. ........... 435/320.1 |
| 2003/0157688 | A1 * | 8/2003 | Von Seggern et al. .... 435/235.1 |

FOREIGN PATENT DOCUMENTS

| WO | WO-98/22609 | 5/1998 |
|---|---|---|
| WO | WO-00/03029 | 1/2000 |

OTHER PUBLICATIONS

Chillon et al., Group D Adenovirus Infect Primary Central Nervous System Cells More Efficiently than Those from Group C 1999, Journal of Virology, vol. 73/No. 3, pp. 2537-2540.*
Zabner et al., A Chimeric Type 2 Adenovirus Vector with a Type 17 Fiber Enhances Gene Transfer to Human Airway Epithelia 1999, Journal of Virology, vol. 73/No. 10, pp. 8689-8695.*
Davidoff et al., Enhanced Neuroblastoma Transduction for an Improved Antitumor Vaccine, 1999, Journal of Surgical Research, vol. 83, pp. 95-99.*
Chillon et al., Genbank Accession # AAD20325, Mar. 10, 1999.*
Appendix A, Sequence alignment between Seq ID No: 12-positions 1-135 and Adenovirus Serotype 17.*
"Recombinant human adenovirus: Targeting to the human transferrin receptor improves gene transfer to brain microcapillary endothelium", *Journal of Virology*, vol. 74, No. 23 (0022-538X),(Dec. 2000),11359-11366.

Anderson, R. D., "A simple method for the rapid generation of recombinant adenovirus vectors", *Gene Therapy*, 7, (2000),pp. 1034-1038.
Arnberg, N., et al., "Fiber Genes of Adenoviruses with Tropism for the Eye and the Genital Tract", *Virology*, 227, (1997),239-244.
Bergelson, J. M., et al., "Isolation of a Common Receptor for Coxsackie B Viruses and Adenoviruses 2 and 5", *Science*, 275, (Feb. 1997),pp. 1320-1323.
Bergelson, J. M., et al., "The Murine CAR Homolog Is a Receptor for Coxsackie B Viruses and Adenovirus", *Journal of Virology*, 72 (1), (Jan. 1998),pp. 415-419.
Chillon, M, et al., "Fiber Human Adenovirus Type 17", *Database Accession* No. Q9WF20, (Nov. 1, 1999).
Chillon, M., et al., "Group D Adenoviruses Infect Primary Central Nervous System Cells More Efficiently Than Those From Group C", *Journal of Virology*, 73(3), (Mar. 1999),pp. 2537-2540.
Crompton, J., et al., "Expression of a foreign epitope on the surface of the adenovirus hexon", *Journal of General Virology*, 75, (1994),pp. 133-139.
Fasbender, A., et al., "Incorporation of Adeonovirus in Calcium Phosphate Precipitates Enhances Gene Transfer to Airway Epithelia In Vitro and In Vivo", *The Journal Of Clinical Investigation*, 102 (1), (Jul. 1998),pp. 184-192.
Freimuth, P., et al., "Coxsackievirus and Adenovirus Receptor Amino-Terminal Immunoglobulin V-Related Domain Binds Adenovirus Type 2 and Fiber Knob from Adenovirus Type 12", *Journal of Virology*, 73 (2), (Feb. 1999),pp. 1392-1398.
Gall, J., et al., "Adenovirus Type 5 and 7 Capsid Chimera: Fiber Replacement Alters Receptor Tropism without Affecting Primary Immune Neutralization Epitopes", *Journal of Virology*, 70 (4), (Apr. 1996),pp. 2116-2123.
Gonzalez, R., et al., "Increaded gene transfer in acute myeloid leukemic cells by an adenovirus vector containing a modified fiber protein", *Gene Therapy*, 6, (1999),pp. 314-320.
Hsu, K. L., et al., "A Monoclonal Antibody Specific for the Cellular Receptor for the Group B Coxsackieviruses", *Journal of Virology*, 62 (5), (May 1988),pp. 1647-1652.
Kirby, I., et al., "Identification of Contact Residues and Definition of the CAR-Binding Site of Adenovirus Type 5 Fiber Protein", *Journal of Virology*, 74 (6), (Mar. 2000),pp. 2804-2813.

(Continued)

*Primary Examiner*—Bruce Campbell
*Assistant Examiner*—Benjamin P Blumel
(74) *Attorney, Agent, or Firm*—Viksnins Harris & Padys PLLP

(57) ABSTRACT

The present invention provides an adenovirus serotype 30 (Ad30) fiber amino acid sequence. The present invention also provides polynucleotides and expression vectors encoding an Ad30 fiber and viral particles and cells containing such expression vectors. The present invention further provides methods of treating genetic diseases or cancers in a mammal using the polynucleotides, polypeptides, expression vectors, viral particles and cells of the present invention.

17 Claims, 7 Drawing Sheets

OTHER PUBLICATIONS

Krasnykh, V., et al., "Characterization of an Adenovirus Vector Containing a Heterlogous Peptide Epitope in the HI Loop of the Fiber Knob", *Journal of Virology*, 72 (3), (Mar. 1998),pp. 1844-1852.

Krasnykh, V. N., et al., "Generation of Recombinant Adenorvirus Vectors with Modified Fibers for Altering Viral Tropism", *Journal of Virology*, 70 (10), (Oct. 1996),pp. 6839-6846.

Law, L K., "Adenovirus serotype 30 fiber does not mediate transduction via the coxsackie-adenovirus receptor", *Journal of Virology*, 76, (Jan. 2002),656-661.

Legrand, V., et al., "Fiberless Recombinant Adenoviruses: Virus Maturation and Infectivity in the Absence of Fiber", *Journal of Virology*, 73 (2), (Feb. 1999),pp. 907-919.

Mastrangeli, Andrea, et al., ""Sero-Switch" Adenovirus-Mediated In Vivo Gene Transfer: Circumvention of Anti-Adenovius Humoral Immune Defenses Against Repeat Adenovirus Vector Administration by Changing the Adenovirus Serotype", *Human Gene Therapy 7*, (Jan. 1, 1996),79-87.

Michael, S. I., et al., "Addition of a short peptide ligand to the adenovirus fiber protein", *Gene Therapy*, 2, (1995),pp. 660-668.

Miyazawa, N., et al., "Fiber Swap between Adenovirus Subgroups B and C Alters Intracellular Trafficking of Adenovirus Gene Transfer Vectors", *Journal of Virology*, 73 (7), (Jul. 1999),pp. 6056-6065.

Mullis, K. G., et al., "Relative Accessibility of N-Acetylglucosamine in Trimers of the Adenovirus Types 2 and 5 Fiber Proteins", *Journal of Virology*, 64 (11), (Nov. 1990),pp. 5317-5323.

Roelvink, P. W., et al., "Identification of a Conserved Receptor-Binding Site on the Fiber Proteins of CAR-Recognizing Adenovirus", *Science*, 286, (Nov. 1999),pp. 1568-1571.

Roelvink, P. W., et al., "The Coxsackiebirus-Adenovirs Receptor Protein Can Function as a Cellular Attachment Protein for Adenovirus Serotypes from Subgroups A, C, D, E, and F", *Journal of Virology*, 72 (10), (Oct. 1998),pp. 7909-7915.

Shayakhmetov, D. M., et al., "Efficient Gene Transfer into Human CD34+ Cells by a retargeted Adenovirus Vector", *Journal of Virology*, 74 (6), (Mar. 2000),pp. 2567-2583.

Stevenson, S. C., et al., "human Adenoviruses Serotypes 3 and 5 Bind to Two Different Cellular Receptors via the Fiber Head Domain", *Journal of Virology*, 69 (5), (May 1995),pp. 2850-2857.

Stevenson, S. C., et al., "Selective Targeting of Human Cells by a Chimeric Adenovirus Vector Containing a Modified Fiber Protein", *Journal of Virology*, 71 (6), (Jun. 1997),pp. 4782-4790.

Tomko, R. P., et al., "HCAR and MCAR: The human and mouse cellular receptors for subgroup C adenovirus and group B coxsackieviruses", *PNAS*, 94, (Apr. 1997),pp. 3352-3356.

Wang, X., et al., "Coxsackievirus and Adenovirus Receptor Cytoplasmic and Transmembrane Domains Are Not Essential for Coxsackievirus and Adenovirus Infection", *Journal of Virology*, 73 (3), (Mar. 1999),pp. 2559-2562.

Wickham, T. J., et al., "Targeting of adenovirus penton base to new receptors through replacement of its RGD motif with other receptor-specific peptide motifs", *Gene Therapy*, 2, (1995),pp. 750-756.

Xia, H., et al., "Recombinant Human Adenovirus: Targeting to the Human Transferrin Receptor Improves Gene Transfer to Brain Microcapillary Endothelium", *Journal of Virology*, 74 (23), (Dec. 2000),pp. 11359-11366.

Zabner, J., et al., "A Chimeric Type 2 Adenovirus Vector with a Type 17 Fiber Enhances Gene Transfer to Human Airway Epithelia", *Journal of Virology*, 73 (10), (Oct. 1999),pp. 8689-8695.

Stevenson et al., Journal of Virology 69:2850-2857 (1995).

Stevenson et al., Journal of Virology 71:4782-4790 (1997).

\* cited by examiner

Figure 1.

```
                     ┌─Tail─────────────────────────────────────────────46┐┌─Shaft──────────────66┐
   D 30 MSKRLRV.ED DFNPVYPYGY ARN.QNIPFL TPPFVSSDGF .KNFPPGV                LSLKLADPIA ITNGDVSLKV
   C  5 M.KRARPSED TFNPVYPYDT ETGPPTVPFL TPPFVSPNGF .QESPPGV                LSLRLSEPLV TSNGMLALKM
   D  9 MSKRLRV.ED DFNPVYPYGY ARN.QNIPFL TPPFVSSDGF .QNFPPGV                LSLKLADPIA IVNGNVSLKV
   D 17 MSKRLRV.ED DFNPVYPYGY ARN.QNIPFL TPPFVSSDGF .KNFPPGV                LSLKLADPIT IANGDVSLKV
   B  3 MAKRARL.ST SFNPVYPYED ESSSQH.PPI NPGFISPDGF TQ.SPNGV                LSLKCVNPLT TASGSLQLKV
                                                                                                135
   30 GGGLTVEQD.   .......... .......... .......... .......... ..........   ..........
    5 GNGLSL.DEA GNLTSQNVTT VSPPLKKTKS NINLEISAPL TVTSEALTVA AAAPLMVAGN   TLTMQSQAPL
    9 GGGLTL.QDG T......... .......... .......... .......... ..........   ..........
   17 GGGLTL.QE. .......... .......... .......... .......... ..........   ..........
    3 GSGLTV.D.. .......... .......... .......... .......... ..........   ..........
                                                                                                205
   30 .......... .......... .......... ....SGNLSV NPKAPLQ... ..........   .VGTDKKLEL
    5 TVHDSKLSIA TQGPLTVSEG KLALQTSGPL TTTDSSTLTI TASPPLTTAT GSLGIDLKEP   IYTQNGKLGL
    9 .......... .......... .......... .....GKLTV NADPPLQ... ..........   .LTNN.KLGI
   17 .......... .......... .......... .....GSLTV DPKAPLQ... ..........   .LANNKKLEL
    3 .......... .......... .......... .......... .......... ......TT..   ..DGSLEENI
                                                                                                275
   30 ALAPPFDVRD ..NKLAILVG DGLKVIDRSI SDLPGLLNY. .......... ..........   ..........
    5 KYGAPLHVTD DLNTLTVATG PGVTINNTSL QTKVTGALGF DSQGNMQLNV AGGLRIDSQN   RRLILDVSYP
    9 ALDAPFDVID ..NKLTLLAG HGLSII.TKE TSTLPGLRN. .......... ..........   ..........
   17 VYVDPFEVSA ..NKLSLKVG HGLKILDDKS AGGLKDLIG. .......... ..........   ..........
    3 KVNTPLTKSN HSINL..PIG NGLQIEQNKL CS........ .......... ..........   ..........
                                                                                                345
   30 .......... .......... .......... .......... .......... ..........   LVVLTGKGIG
    5 FDAQNQLNLR LGQGPLFINS AHNLDINYNK GLYLFTASNN SKKLEVNLST AKGLMFDATA   IAINAGDGLE
    9 .......... .......... .......... .......... .......... .........T   LVVLTGKGIG
   17 .......... .......... .......... .......... .......... .........K   LVVLTGKGIG
    3 .......... .......... .......... .......... .......... ..........   ..........
                                                                            400*         410*
   30 NEELKNDDGS NKGVGLCVRI G.E....... ....GGGLTF DDKGYLVAWN NKHDIRT        LWTTLDPSPN
    5 FG..SPNAPN TNPLKTKIGH GLEFDSNKAM VPKLGTGLSF DSTGAITVGN KNNDKLT        LWTTPAPSPN
    9 TESTDNGG.. ..TVCVRV.. G.E....... ....GGGLSF NNDGDLVAFN KKEDKRT        LWTTPDTSPN
   17 TENLQNTDGS SRGIGISVRA .......... ....REGLTF DNDGYLVAWN PKYDTRT        LWTTPDTSPN
    3 .......... .......... .......... ..KLGNGLTF DSSNSIALKN N.....T        LWTGPKPEAN
                                                                                                471
   30 CKID...IEK DSKLTLVLTK CGSQILANVS LIIVNGKFKI LNNKTDP.SL PKSFNIKLLF   DQNGVLLENS
    5 CRLN...AEK DAKLTLVLTK CGSQILATVS VLAV.K.... .GSLAPISGT VQSAHLIIRF   DENGVLLNNS
    9 CKID...QDK DSKLTLVLTK CGSQILANVS LIVVDGKYKI INNNTQP..A LKGFTIKLLF   DENGVLMESS
   17 CRID...KEK DSKLTLVLTK CGSQILANVS LIVVSGKYQY IDHATNP..T LKSFKIKLLF   DNKGVLLPSS
    3 CIIEYGKQNP DSKLTLILVK NGGIVNGYVT LMGASDYVNT LFKNKNV... ..SINVELYF   DATGHILPDS
                                                                                                526
   30 N........I EKQYLNFRSG DSILPEPYKN AIGFMPNLLA YAKATTDQSK IY...ARNTI   YGNIYLDNQP
    5 F........L DPEWNFRNG  ILTEGTAYTN AVGFMPNLSA YPKSHGK.T. .....AKSNI   VSQVYLNGDK
    9 N........L GKSYWNFRNE NSIMSTAYEK AIGFMPNLVA YPKPTAG.SK KY...ARDIV   YGNIYLGGKP
   17 N........L DSTYWNFRSD NLTVSEAYKN AVEFMPNLVA YPKPTTG.SK KY...ARDIV   YGNIYLGGLA
    3 SSLKTDLELK YKQTADF... .........S ARGFMPSTTA YPFVLPN.AG TH...NENYI   FGQCYYKASD
                                                                                                582*
   30 YN..PVVIKI TFNNEAD... ....SAYSIT FNYSWTKD.Y DNIPFDSTSF TFSYIAQE
    5 TK..PVTLTI TLNGTQETGD TT.PSAYSMS FSWDWSGHNY INEIFATSSY TFSYIAQE       Knob
    9 DQ..PVTIKT TFNQETG... ....CEYSIT FDFSWAKT.Y VNVEFETTSF TFSYIAQE
   17 YQ..PVVIKV TFNEEAD... ....SAYSIT FEFVWNKE.Y ARVEFETTSF TFSYIAQQ
    3 GALFPLEVTV MLNKRLPDSR TSYVMTFLWS LNAGLAPET. TQATLITSPF TFSYIREDD
```

*numbers refer to Ad5 amino acid sequence

Figure 2.

Amino Acids within Ad5 fiber Important and <u>Critical</u> for CAR Binding

<u>Binds CAR?</u>

| | 401 (Ad5) | | | 473 (Ad5) |
|---|---|---|---|---|
| D | 30 LWTTLDPSPNCKID | ? | 30 | GDSILPEPYKNAIGFMPN |
| C | 5 LWTTPAP<u>SP</u>NCRLN | Yes | 5 | LDPE<u>Y</u>WNFRNGD<u>L</u>TEGTA |
| C | 2 LWTTPDPSPNCRIH | Yes | 2 | LKKHYWNFRNGNSTNANP |
| D | 9 LWTTPDTSPNCKID | Yes/No | 9 | LGKSYWNFRNENSIMSTA |
| D | 17 LWTTPDTSPNCKID | Yes | 17 | LDSTYWNFRSDNLTVSEA |
| B | 3 LWTGPKPEANCIIE | No | 3 | . . . . . . . . . .SARGFMPS |

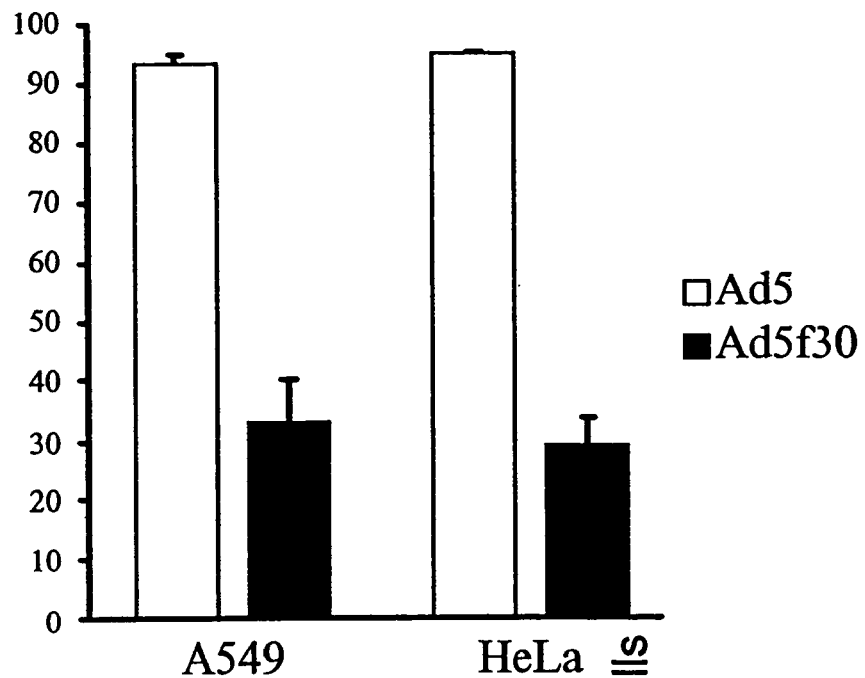
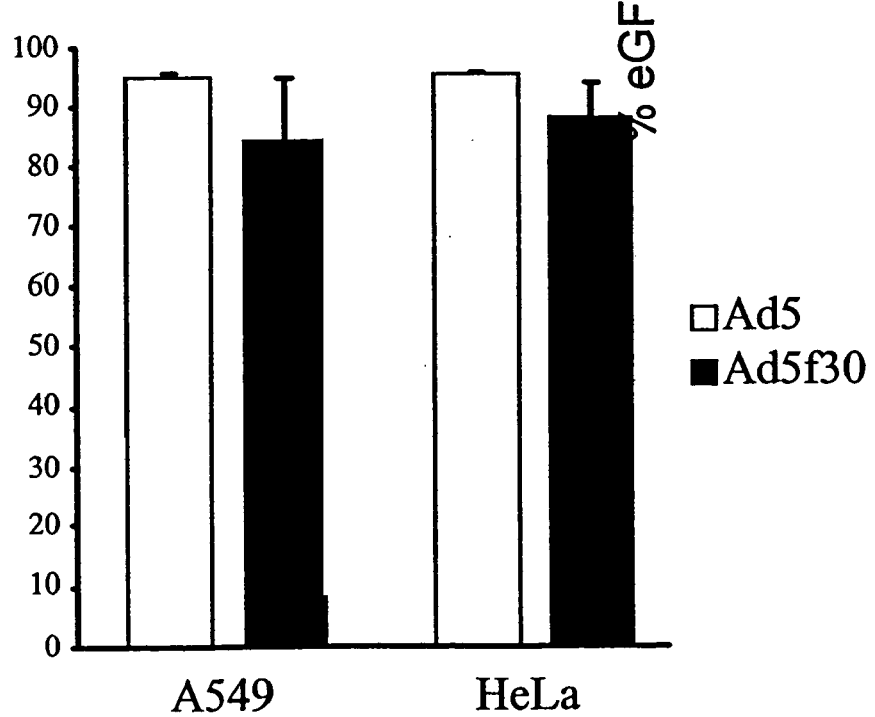

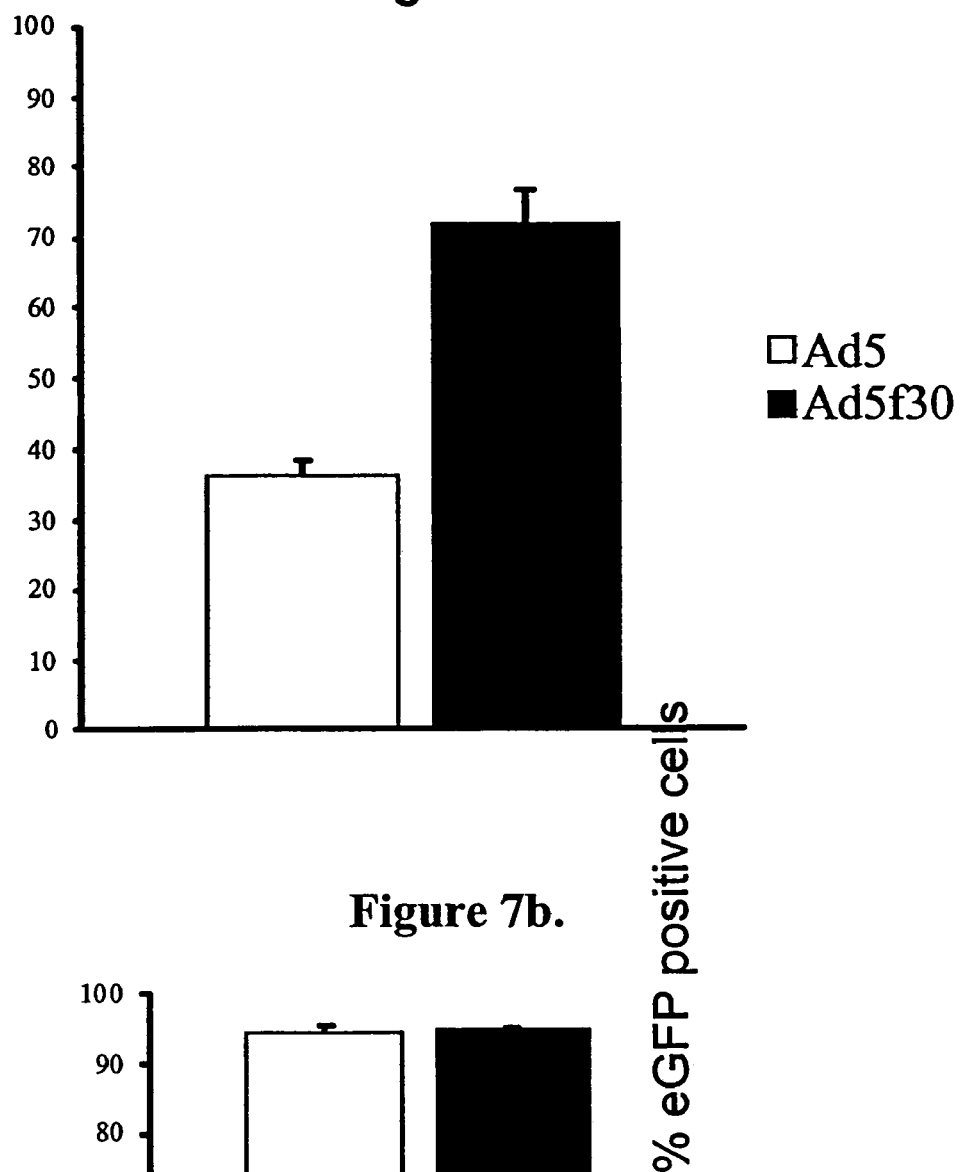
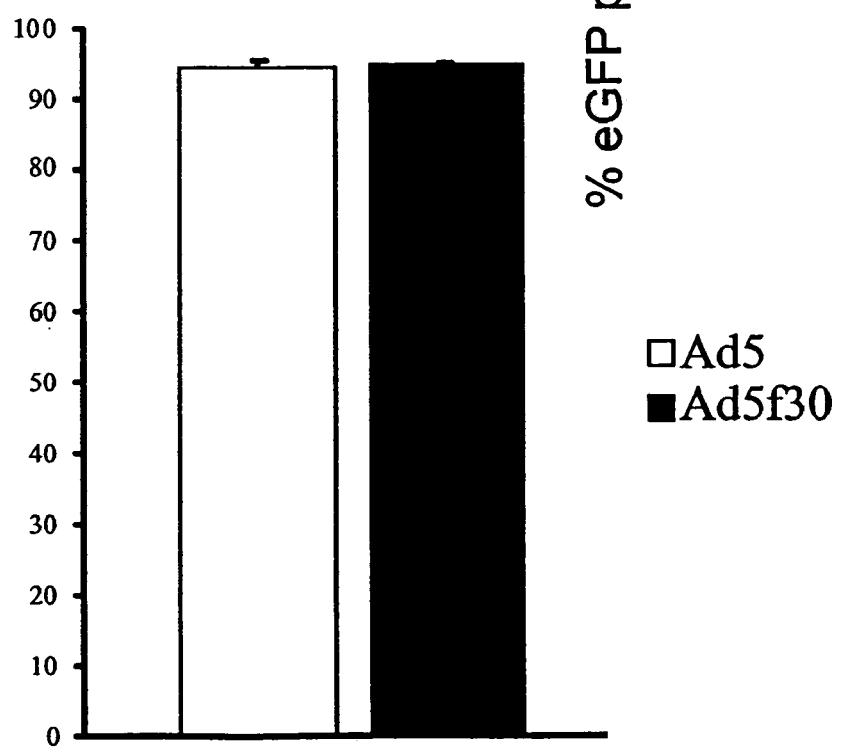

SEQUENCE LISTING

```
<160> NUMBER OF SEQ ID NOS: 24

<210> SEQ ID NO 1
<211> LENGTH: 371
<212> TYPE: PRT
<213> ORGANISM: Adenovirus

<400> SEQUENCE: 1

Met Ser Lys Arg Leu Arg Val Glu Asp Asp Phe Asn Pro Val Tyr Pro
1               5                   10                  15

Tyr Gly Tyr Ala Arg Asn Gln Asn Ile Pro Phe Leu Thr Pro Pro Phe
            20                  25                  30

Val Ser Ser Asp Gly Phe Lys Asn Phe Pro Pro Gly Val Leu Ser Leu
        35                  40                  45

Lys Leu Ala Asp Pro Ile Ala Ile Thr Asn Gly Asp Val Ser Leu Lys
```

-continued

```
            50                  55                  60
Val Gly Gly Leu Thr Val Glu Gln Asp Ser Gly Asn Leu Ser Val
 65                  70                  75                  80

Asn Pro Lys Ala Pro Leu Gln Val Gly Thr Asp Lys Lys Leu Glu Leu
                 85                  90                  95

Ala Leu Ala Pro Pro Phe Asp Val Arg Asp Asn Lys Leu Ala Ile Leu
                100                 105                 110

Val Gly Asp Gly Leu Lys Val Ile Asp Arg Ser Ile Ser Asp Leu Pro
                115                 120                 125

Gly Leu Leu Asn Tyr Leu Val Val Leu Thr Gly Lys Gly Ile Gly Asn
        130                 135                 140

Glu Glu Leu Lys Asn Asp Asp Gly Ser Asn Lys Gly Val Gly Leu Cys
145                 150                 155                 160

Val Arg Ile Gly Glu Gly Gly Gly Leu Thr Phe Asp Asp Lys Gly Tyr
                165                 170                 175

Leu Val Ala Trp Asn Asn Lys His Asp Ile Arg Thr Leu Trp Thr Thr
                180                 185                 190

Leu Asp Pro Ser Pro Asn Cys Lys Ile Asp Ile Glu Lys Asp Ser Lys
                195                 200                 205

Leu Thr Leu Val Leu Thr Lys Cys Gly Ser Gln Ile Leu Ala Asn Val
        210                 215                 220

Ser Leu Ile Ile Val Asn Gly Lys Phe Lys Ile Leu Asn Asn Lys Thr
225                 230                 235                 240

Asp Pro Ser Leu Pro Lys Ser Phe Asn Ile Lys Leu Leu Phe Asp Gln
                245                 250                 255

Asn Gly Val Leu Leu Glu Asn Ser Asn Ile Glu Lys Gln Tyr Leu Asn
                260                 265                 270

Phe Arg Ser Gly Asp Ser Ile Leu Pro Glu Pro Tyr Lys Asn Ala Ile
                275                 280                 285

Gly Phe Met Pro Asn Leu Leu Ala Tyr Ala Lys Ala Thr Thr Asp Gln
        290                 295                 300

Ser Lys Ile Tyr Ala Arg Asn Thr Ile Tyr Gly Asn Ile Tyr Leu Asp
305                 310                 315                 320

Asn Gln Pro Tyr Asn Pro Val Val Ile Lys Ile Thr Phe Asn Asn Glu
                325                 330                 335

Ala Asp Ser Ala Tyr Ser Ile Thr Phe Asn Tyr Ser Trp Thr Lys Asp
                340                 345                 350

Tyr Asp Asn Ile Pro Phe Asp Ser Thr Ser Phe Thr Phe Ser Tyr Ile
                355                 360                 365

Ala Gln Glu
    370
```

<210> SEQ ID NO 2
<211> LENGTH: 362
<212> TYPE: PRT
<213> ORGANISM: Adenovirus

<400> SEQUENCE: 2

```
Met Ser Lys Arg Leu Arg Val Glu Asp Asp Phe Asn Pro Val Tyr Pro
  1               5                  10                  15

Tyr Gly Tyr Ala Arg Asn Gln Asn Ile Pro Phe Leu Thr Pro Pro Phe
                 20                  25                  30

Val Ser Ser Asp Gly Phe Gln Asn Phe Pro Pro Gly Val Leu Ser Leu
         35                  40                  45
```

```
Lys Leu Ala Asp Pro Ile Ala Ile Val Asn Gly Asn Val Ser Leu Lys
 50                  55                  60

Val Gly Gly Gly Leu Thr Leu Gln Asp Gly Thr Gly Lys Leu Thr Val
 65                  70                  75                  80

Asn Ala Asp Pro Pro Leu Gln Leu Thr Asn Asn Lys Leu Gly Ile Ala
                 85                  90                  95

Leu Asp Ala Pro Phe Asp Val Ile Asp Asn Lys Leu Thr Leu Leu Ala
                100                 105                 110

Gly His Gly Leu Ser Ile Ile Thr Lys Glu Thr Ser Thr Leu Pro Gly
             115                 120                 125

Leu Arg Asn Thr Leu Val Val Leu Thr Gly Lys Gly Ile Gly Thr Glu
130                 135                 140

Ser Thr Asp Asn Gly Gly Thr Val Cys Val Arg Val Gly Glu Gly Gly
145                 150                 155                 160

Gly Leu Ser Phe Asn Asn Asp Gly Asp Leu Val Ala Phe Asn Lys Lys
                165                 170                 175

Glu Asp Lys Arg Thr Leu Trp Thr Thr Pro Asp Thr Ser Pro Asn Cys
                180                 185                 190

Lys Ile Asp Gln Asp Lys Asp Ser Lys Leu Thr Leu Val Leu Thr Lys
            195                 200                 205

Cys Gly Ser Gln Ile Leu Ala Asn Val Ser Leu Ile Val Val Asp Gly
210                 215                 220

Lys Tyr Lys Ile Ile Asn Asn Asn Thr Gln Pro Ala Leu Lys Gly Phe
225                 230                 235                 240

Thr Ile Lys Leu Leu Phe Asp Glu Asn Gly Val Leu Met Glu Ser Ser
                245                 250                 255

Asn Leu Gly Lys Ser Tyr Trp Asn Phe Arg Asn Glu Asn Ser Ile Met
            260                 265                 270

Ser Thr Ala Tyr Glu Lys Ala Ile Gly Phe Met Pro Asn Leu Val Ala
            275                 280                 285

Tyr Pro Lys Pro Thr Ala Gly Ser Lys Lys Tyr Ala Arg Asp Ile Val
290                 295                 300

Tyr Gly Asn Ile Tyr Leu Gly Gly Lys Pro Asp Gln Pro Val Thr Ile
305                 310                 315                 320

Lys Thr Thr Phe Asn Gln Glu Thr Gly Cys Glu Tyr Ser Ile Thr Phe
                325                 330                 335

Asp Phe Ser Trp Ala Lys Thr Tyr Val Asn Val Glu Phe Glu Thr Thr
            340                 345                 350

Ser Phe Thr Phe Ser Tyr Ile Ala Gln Glu
            355                 360
```

<210> SEQ ID NO 3
<211> LENGTH: 366
<212> TYPE: PRT
<213> ORGANISM: Adenovirus

<400> SEQUENCE: 3

```
Met Ser Lys Arg Leu Arg Val Glu Asp Asp Phe Asn Pro Val Tyr Pro
 1               5                  10                  15

Tyr Gly Tyr Ala Arg Asn Gln Asn Ile Pro Phe Leu Thr Pro Pro Phe
                 20                  25                  30

Val Ser Ser Asp Gly Phe Lys Asn Phe Pro Pro Gly Val Leu Ser Leu
             35                  40                  45

Lys Leu Ala Asp Pro Ile Thr Ile Ala Asn Gly Asp Val Ser Leu Lys
 50                  55                  60
```

```
Val Gly Gly Gly Leu Thr Leu Gln Glu Gly Ser Met Thr Val Asp Pro
 65                  70                  75                  80

Lys Ala Pro Leu Gln Leu Ala Asn Asn Lys Lys Leu Glu Leu Val Tyr
                 85                  90                  95

Val Asp Pro Phe Glu Val Ser Ala Asn Lys Leu Ser Leu Lys Val Gly
            100                 105                 110

His Gly Leu Lys Ile Leu Asp Asp Lys Ser Ala Gly Gly Leu Lys Asp
        115                 120                 125

Leu Ile Gly Lys Leu Val Val Leu Thr Gly Lys Gly Ile Gly Thr Glu
    130                 135                 140

Asn Leu Gln Asn Thr Asp Gly Ser Ser Arg Gly Ile Gly Ile Ser Val
145                 150                 155                 160

Arg Ala Arg Glu Gly Leu Thr Phe Asp Asn Asp Gly Tyr Leu Val Ala
                165                 170                 175

Trp Asn Pro Lys Tyr Asp Thr Arg Thr Leu Trp Thr Thr Pro Asp Thr
            180                 185                 190

Ser Pro Asn Cys Arg Ile Asp Lys Glu Lys Asp Ser Lys Leu Thr Leu
        195                 200                 205

Val Leu Thr Lys Cys Gly Ser Gln Ile Leu Ala Asn Val Ser Leu Ile
    210                 215                 220

Val Val Ser Gly Lys Tyr Gln Tyr Ile Asp His Ala Thr Asn Pro Thr
225                 230                 235                 240

Leu Lys Ser Phe Lys Ile Lys Leu Leu Phe Asp Asn Lys Gly Val Leu
                245                 250                 255

Leu Pro Ser Ser Asn Leu Asp Ser Thr Tyr Trp Asn Phe Arg Ser Asp
            260                 265                 270

Asn Leu Thr Val Ser Glu Ala Tyr Lys Asn Ala Val Glu Phe Met Pro
        275                 280                 285

Asn Leu Val Ala Tyr Pro Lys Pro Thr Thr Gly Ser Lys Lys Tyr Ala
    290                 295                 300

Arg Asp Ile Val Tyr Gly Asn Ile Tyr Leu Gly Gly Leu Ala Tyr Gln
305                 310                 315                 320

Pro Val Val Ile Lys Val Thr Phe Asn Glu Glu Ala Asp Ser Ala Tyr
                325                 330                 335

Ser Ile Thr Phe Glu Phe Val Trp Asn Lys Glu Tyr Ala Arg Val Glu
            340                 345                 350

Phe Glu Thr Thr Ser Phe Thr Phe Ser Tyr Ile Ala Gln Gln
        355                 360                 365

<210> SEQ ID NO 4
<211> LENGTH: 362
<212> TYPE: PRT
<213> ORGANISM: Adenovirus

<400> SEQUENCE: 4

Met Ser Lys Arg Leu Arg Val Glu Asp Asp Phe Asn Pro Val Tyr Pro
 1               5                  10                  15

Tyr Gly Tyr Ala Arg Asn Gln Asn Ile Pro Phe Leu Thr Pro Pro Phe
                20                  25                  30

Val Ser Ser Asp Gly Phe Gln Asn Phe Pro Pro Gly Val Leu Ser Leu
            35                  40                  45

Lys Leu Ala Asp Pro Ile Ala Ile Val Asn Gly Asn Val Ser Leu Lys
        50                  55                  60

Val Gly Gly Gly Leu Thr Leu Gln Asp Gly Thr Gly Lys Leu Thr Val
```

```
                65                  70                  75                  80
Asn Ala Asp Pro Pro Leu Gln Leu Thr Asn Asn Lys Leu Gly Ile Ala
                    85                  90                  95

Leu Asp Ala Pro Phe Asp Val Ile Asp Asn Lys Leu Thr Leu Leu Ala
                100                 105                 110

Gly His Gly Leu Ser Ile Ile Thr Lys Glu Thr Ser Thr Leu Pro Gly
                115                 120                 125

Leu Arg Asn Thr Leu Val Val Leu Thr Gly Lys Gly Ile Gly Thr Glu
            130                 135                 140

Ser Thr Asp Asn Gly Gly Thr Val Cys Val Arg Val Gly Glu Gly Gly
145                 150                 155                 160

Gly Leu Ser Phe Asn Asn Asp Gly Asp Leu Val Ala Phe Asn Lys Lys
                165                 170                 175

Glu Asp Lys Arg Thr Leu Trp Thr Thr Pro Asp Thr Ser Pro Asn Cys
                180                 185                 190

Lys Ile Asp Gln Asp Lys Asp Ser Lys Leu Thr Leu Val Leu Thr Lys
                195                 200                 205

Cys Gly Ser Gln Ile Leu Ala Asn Val Ser Leu Ile Val Val Asp Gly
            210                 215                 220

Lys Tyr Lys Ile Ile Asn Asn Asn Thr Gln Pro Ala Leu Lys Gly Phe
225                 230                 235                 240

Thr Ile Lys Leu Leu Phe Asp Glu Asn Gly Val Leu Met Glu Ser Ser
                245                 250                 255

Asn Leu Gly Lys Ser Tyr Trp Asn Phe Arg Asn Glu Asn Ser Ile Met
                260                 265                 270

Ser Thr Ala Tyr Glu Lys Ala Ile Gly Phe Met Pro Asn Leu Val Ala
            275                 280                 285

Tyr Pro Lys Pro Thr Ala Gly Ser Lys Lys Tyr Ala Arg Asp Ile Val
290                 295                 300

Tyr Gly Asn Ile Tyr Leu Gly Gly Lys Pro Asp Gln Pro Val Thr Ile
305                 310                 315                 320

Lys Thr Thr Phe Asn Gln Glu Thr Gly Cys Glu Tyr Ser Ile Thr Phe
                325                 330                 335

Asp Phe Ser Trp Ala Lys Thr Tyr Val Asn Val Glu Phe Glu Thr Thr
            340                 345                 350

Ser Phe Thr Phe Ser Tyr Ile Ala Gln Glu
            355                 360

<210> SEQ ID NO 5
<211> LENGTH: 581
<212> TYPE: PRT
<213> ORGANISM: Adenovirus

<400> SEQUENCE: 5

Met Lys Arg Ala Arg Pro Ser Glu Asp Thr Phe Asn Pro Val Tyr Pro
  1               5                  10                  15

Tyr Asp Thr Glu Thr Gly Pro Pro Thr Val Pro Phe Leu Thr Pro Pro
                20                  25                  30

Phe Val Ser Pro Asn Gly Phe Gln Glu Ser Pro Pro Gly Val Leu Ser
            35                  40                  45

Leu Arg Leu Ser Glu Pro Leu Val Thr Ser Asn Gly Met Leu Ala Leu
        50                  55                  60

Lys Met Gly Asn Gly Leu Ser Leu Asp Glu Ala Gly Asn Leu Thr Ser
65                  70                  75                  80
```

-continued

```
Gln Asn Val Thr Thr Val Ser Pro Pro Leu Lys Lys Thr Lys Ser Asn
                85                  90                  95
Ile Asn Leu Glu Ile Ser Ala Pro Leu Thr Val Thr Ser Glu Ala Leu
            100                 105                 110
Thr Val Ala Ala Ala Pro Leu Met Val Ala Gly Asn Thr Leu Thr
        115                 120                 125
Met Gln Ser Gln Ala Pro Leu Thr Val His Asp Ser Lys Leu Ser Ile
    130                 135                 140
Ala Thr Gln Gly Pro Leu Thr Val Ser Glu Gly Lys Leu Ala Leu Gln
145                 150                 155                 160
Thr Ser Gly Pro Leu Thr Thr Thr Asp Ser Ser Thr Leu Thr Ile Thr
                165                 170                 175
Ala Ser Pro Pro Leu Thr Thr Ala Thr Gly Ser Leu Gly Ile Asp Leu
                180                 185                 190
Lys Glu Pro Ile Tyr Thr Gln Asn Gly Lys Leu Gly Leu Lys Tyr Gly
            195                 200                 205
Ala Pro Leu His Val Thr Asp Asp Leu Asn Thr Leu Thr Val Ala Thr
        210                 215                 220
Gly Pro Gly Val Thr Ile Asn Asn Thr Ser Leu Gln Thr Lys Val Thr
225                 230                 235                 240
Gly Ala Leu Gly Phe Asp Ser Gln Gly Asn Met Gln Leu Asn Val Ala
                245                 250                 255
Gly Gly Leu Arg Ile Asp Ser Gln Asn Arg Arg Leu Ile Leu Asp Val
            260                 265                 270
Ser Tyr Pro Phe Asp Ala Gln Asn Gln Leu Asn Leu Arg Leu Gly Gln
        275                 280                 285
Gly Pro Leu Phe Ile Asn Ser Ala His Asn Leu Asp Ile Asn Tyr Asn
    290                 295                 300
Lys Gly Leu Tyr Leu Phe Thr Ala Ser Asn Asn Ser Lys Lys Leu Glu
305                 310                 315                 320
Val Asn Leu Ser Thr Ala Lys Gly Leu Met Phe Asp Ala Thr Ala Ile
                325                 330                 335
Ala Ile Asn Ala Gly Asp Gly Leu Glu Phe Gly Ser Pro Asn Ala Pro
            340                 345                 350
Asn Thr Asn Pro Leu Lys Thr Lys Ile Gly His Gly Leu Glu Phe Asp
        355                 360                 365
Ser Asn Lys Ala Met Val Pro Lys Leu Gly Thr Gly Leu Ser Phe Asp
    370                 375                 380
Ser Thr Gly Ala Ile Thr Val Gly Asn Lys Asn Asn Asp Lys Leu Thr
385                 390                 395                 400
Leu Trp Thr Thr Pro Ala Pro Ser Pro Asn Cys Arg Leu Asn Ala Glu
                405                 410                 415
Lys Asp Ala Lys Leu Thr Leu Val Leu Thr Lys Cys Gly Ser Gln Ile
            420                 425                 430
Leu Ala Thr Val Ser Val Leu Ala Val Lys Gly Ser Leu Ala Pro Ile
        435                 440                 445
Ser Gly Thr Val Gln Ser Ala His Leu Ile Ile Arg Phe Asp Glu Asn
    450                 455                 460
Gly Val Leu Leu Asn Asn Ser Phe Leu Asp Pro Glu Tyr Trp Asn Phe
465                 470                 475                 480
Arg Asn Gly Asp Leu Thr Glu Gly Thr Ala Tyr Thr Asn Ala Val Gly
                485                 490                 495
Phe Met Pro Asn Leu Ser Ala Tyr Pro Lys Ser His Gly Lys Thr Ala
```

```
                500             505             510
Lys Ser Asn Ile Val Ser Gln Val Tyr Leu Asn Gly Asp Lys Thr Lys
        515                 520                 525

Pro Val Thr Leu Thr Ile Thr Leu Asn Gly Thr Gln Glu Thr Gly Asp
    530                 535                 540

Thr Thr Pro Ser Ala Tyr Ser Met Ser Phe Ser Trp Asp Trp Ser Gly
545                 550                 555                 560

His Asn Tyr Ile Asn Glu Ile Phe Ala Thr Ser Ser Tyr Thr Phe Ser
                565                 570                 575

Tyr Ile Ala Gln Glu
            580

<210> SEQ ID NO 6
<211> LENGTH: 32
<212> TYPE: DNA
<213> ORGANISM: Adenovirus

<400> SEQUENCE: 6
cgggatccgc caccatgtca aagaggctcc gg                                    32

<210> SEQ ID NO 7
<211> LENGTH: 28
<212> TYPE: DNA
<213> ORGANISM: Adenovirus

<400> SEQUENCE: 7
cgggatcctr attcttgggc yatatagg                                         28

<210> SEQ ID NO 8
<211> LENGTH: 27
<212> TYPE: DNA
<213> ORGANISM: Adenovirus

<400> SEQUENCE: 8
cgcggatccg cgatgaagcg cgcaaga                                          27

<210> SEQ ID NO 9
<211> LENGTH: 36
<212> TYPE: DNA
<213> ORGANISM: Adenovirus

<400> SEQUENCE: 9
gattgggtca gccagtttca agagagtac cccagg                                 36

<210> SEQ ID NO 10
<211> LENGTH: 33
<212> TYPE: DNA
<213> ORGANISM: Adenovirus

<400> SEQUENCE: 10
cctggggtac tctctttgaa actggctgac cca                                   33

<210> SEQ ID NO 11
<211> LENGTH: 27
<212> TYPE: DNA
<213> ORGANISM: Adenovirus

<400> SEQUENCE: 11
aaaactagtt cattcttggg cgatata                                          27

<210> SEQ ID NO 12
```

<211> LENGTH: 1116
<212> TYPE: DNA
<213> ORGANISM: Adenovirus

<400> SEQUENCE: 12

```
atgtcaaaga ggctccgggt ggaagatgac ttcaaccccg tctacccta tggctacgcg      60
cggaatcaga atatccctt ccttactccc ccctttgtct catccgatgg attcaaaaac     120
ttcccacctg ggtcctgtc actcaaactg gctgacccaa tcgccatcac taatggggat     180
gtctcactca aggtgggagg gggactaact gtggaacaag atagtggaaa cctaagtgta     240
aaccctaagg ctccattgca agttggaaca gacaaaaaac tggaattggc tttagcacct     300
ccatttgatg tcagagataa caagctagct attctagtag agatggatt aaaggtaata     360
gatagatcaa tatctgattt gccaggtttg ttaaactatc ttgtagtttt gactggcaaa     420
ggaattggaa atgaagaatt aaaaaatgac gatggtagca ataaaggagt cggtttatgt     480
gtgagaattg gagaaggagg tggtttaact tttgatgata aaggttattt agtagcatgg     540
aacaataaac atgacatccg cacactttgg acaactttag acccttctcc aaattgtaag     600
atagatatag aaaaagactc aaaactaact ttggtactga caaagtgcgg aagtcagatt     660
ttggcaaatg tatctctaat tatagtcaac ggaaagttca agatccttaa taacaaaaca     720
gacccatccc tacctaaatc atttaacatc aaactactgt ttgatcaaaa tggagttcta     780
ttggaaaatt caaacattga aaacagtac ctaaacttta gaagtggaga ctctattctt     840
ccagagccat ataaaaatgc aattggattt atgcctaatt tactagctta tgctaaagct     900
acaactgatc agtctaaaat ttatgcaagg aacactatat atggaaatat ctacttagat     960
aatcagccat ataatccagt tgtaattaaa attactttta ataatgaagc agatagtgct    1020
tattctatca ctttttaacta ttcatggacc aaggactatg acaatatccc ttttgattct    1080
acttcattta ccttctccta tatcgcccaa gaatga                              1116
```

<210> SEQ ID NO 13
<211> LENGTH: 14
<212> TYPE: PRT
<213> ORGANISM: Adenovirus

<400> SEQUENCE: 13

Leu Trp Thr Thr Leu Asp Pro Ser Pro Asn Cys Lys Ile Asp
 1               5                  10

<210> SEQ ID NO 14
<211> LENGTH: 14
<212> TYPE: PRT
<213> ORGANISM: Adenovirus

<400> SEQUENCE: 14

Leu Trp Thr Thr Pro Ala Pro Ser Pro Asn Cys Arg Leu Asn
 1               5                  10

<210> SEQ ID NO 15
<211> LENGTH: 14
<212> TYPE: PRT
<213> ORGANISM: Adenovirus

<400> SEQUENCE: 15

Leu Trp Thr Thr Pro Asp Pro Ser Pro Asn Cys Arg Ile His
 1               5                  10

<210> SEQ ID NO 16

```
<211> LENGTH: 14
<212> TYPE: PRT
<213> ORGANISM: Adenovirus

<400> SEQUENCE: 16

Leu Trp Thr Thr Pro Asp Thr Ser Pro Asn Cys Lys Ile Asp
1               5                   10

<210> SEQ ID NO 17
<211> LENGTH: 14
<212> TYPE: PRT
<213> ORGANISM: Adenovirus

<400> SEQUENCE: 17

Leu Trp Thr Thr Pro Asp Thr Ser Pro Asn Cys Lys Ile Asp
1               5                   10

<210> SEQ ID NO 18
<211> LENGTH: 14
<212> TYPE: PRT
<213> ORGANISM: Adenovirus

<400> SEQUENCE: 18

Leu Trp Thr Gly Pro Lys Pro Glu Ala Asn Cys Ile Ile Glu
1               5                   10

<210> SEQ ID NO 19
<211> LENGTH: 18
<212> TYPE: PRT
<213> ORGANISM: Adenovirus

<400> SEQUENCE: 19

Gly Asp Ser Ile Leu Pro Glu Pro Tyr Lys Asn Ala Ile Gly Phe Met
1               5                   10                  15

Pro Asn

<210> SEQ ID NO 20
<211> LENGTH: 18
<212> TYPE: PRT
<213> ORGANISM: Adenovirus

<400> SEQUENCE: 20

Leu Asp Pro Glu Tyr Trp Asn Phe Arg Asn Gly Asp Leu Thr Glu Gly
1               5                   10                  15

Thr Ala

<210> SEQ ID NO 21
<211> LENGTH: 18
<212> TYPE: PRT
<213> ORGANISM: Adenovirus

<400> SEQUENCE: 21

Leu Lys Lys His Tyr Trp Asn Phe Arg Asn Gly Asn Ser Thr Asn Ala
1               5                   10                  15

Asn Pro

<210> SEQ ID NO 22
<211> LENGTH: 18
<212> TYPE: PRT
<213> ORGANISM: Adenovirus

<400> SEQUENCE: 22

Leu Gly Lys Ser Tyr Trp Asn Phe Arg Asn Glu Asn Ser Ile Met Ser
```

-continued

```
                1               5              10              15
Thr Ala

<210> SEQ ID NO 23
<211> LENGTH: 18
<212> TYPE: PRT
<213> ORGANISM: Adenovirus

<400> SEQUENCE: 23

Leu Asp Ser Thr Tyr Trp Asn Phe Arg Ser Asp Asn Leu Thr Val Ser
 1               5                  10                  15

Glu Ala

<210> SEQ ID NO 24
<211> LENGTH: 8
<212> TYPE: PRT
<213> ORGANISM: Adenovirus

<400> SEQUENCE: 24

Ser Ala Arg Gly Phe Met Pro Ser
 1               5
```

ADENOVIRUS SEROTYPE 30 (AD30)

RELATED APPLICATION

This is a divisional application of U.S. application Ser. No. 09/758,008 filed Jan. 9, 2001, which issued as U.S. Pat. No. 6,635,466, which application is incorporated herein by reference.

U.S. GOVERNMENT RIGHTS Portions of the present invention were made with support of the United States Government via a grant from the National Institutes of Health under grant number HD33531. The U.S. Government therefore may have certain rights in the invention.

BACKGROUND OF THE INVENTION

Gene transfer for the correction of inborn errors of metabolism and neurodegenerative diseases of the central nervous system (CNS), and for the treatment of cancer has been accomplished with recombinant adenoviral vectors. High particle doses, however, are required for efficacy in mice and rats, and for the infection of large numbers of cells in monkeys. The delivery of such high particle loads has the negative side effect of inducing an immune response in vivo. Thus, gene transfer to brain tissues with adenovirus type 2 (Ad2) or Ad5 vectors is inefficient, which is also true for endothelia, smooth muscle, and differentiated airway epithelia. Methods that improve the efficiency of adenovirus-mediated gene transfer to cells of the CNS, or other target cells such as tumor cells, could reduce the particle load required to achieve sufficient levels of transduction. Improved efficiency could then reduce toxicity and increase the therapeutic index.

There is a continuing need for vehicles and methods for efficient adenovirus-mediated gene transfer of nucleic acids or proteins to cells, such as cells of the CNS or tumor cells.

SUMMARY OF THE INVENTION

The present invention provides adenovirus serotype 30 (Ad30) fiber proteins, such as the polypeptide encoded by SEQ ID NO:1. The present invention also provides a polynucleotide encoding such Ad30 fiber protein, such as the polynucleotide encoded by SEQ ID NO:12. As used herein, the term "fiber protein" includes variants or biologically active or inactive fragments of this polypeptide. A "variant" of the polypeptide is a fiber protein that is not completely identical to a native fiber protein. A variant fiber protein can be obtained by altering the amino acid sequence by insertion, deletion or substitution of one or more amino acid. The amino acid sequence of the protein is modified, for example by substitution, to create a polypeptide having substantially the same or improved qualities as compared to the native polypeptide. The substitution may be a conserved substitution. A "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall peptide retains its spacial conformation but has altered biological activity. For example, common conserved changes might be Asp to Glu, Asn or Gln; His to Lys, Arg or Phe; Asn to Gln, Asp or Glu and Ser to Cys, Thr or Gly. Alanine is commonly used to substitute for other amino acids. The 20 essential amino acids can be grouped as follows: alanine, valine, leucine, isoleucine, proline, phenylalanine, tryptophan and methionine having nonpolar side chains; glycine, serine, threonine, cystine, tyrosine, asparagine and glutamine having uncharged polar side chains; aspartate and glutamate having acidic side chains; and lysine, arginine, and histidine having basic side chains. Stryer, L. *Biochemistry* (2d edition) W. H. Freeman and Co. San Francisco (1981), p. 14-15; Lehninger, A. *Biochemistry* (2d ed., 1975), p. 73-75.

It is known that variant polypeptides can be obtained based on substituting certain amino acids for other amino acids in the polypeptide structure in order to modify or improve biological activity. For example, through substitution of alternative amino acids, small conformational changes may be conferred upon a polypeptide that result in increased bioactivity. Alternatively, amino acid substitutions in certain polypeptides may be used to provide residues that may then be linked to other molecules to provide peptide-molecule conjugates that retain sufficient properties of the starting polypeptide to be useful for other purposes.

One can use the hydropathic index of amino acids in conferring interactive biological function on a polypeptide, wherein it is found that certain amino acids may be substituted for other amino acids having similar hydropathic indices and still retain a similar biological activity. Alternatively, substitution of like amino acids may be made on the basis of hydrophilicity, particularly where the biological function desired in the polypeptide to be generated in intended for use in immunological embodiments. The greatest local average hydrophilicity of a protein, as governed by the hydrophilicity of its adjacent amino acids, correlates with its immunogenicity. U.S. Pat. No. 4,554,101. Accordingly, it is noted that substitutions can be made based on the hydrophilicity assigned to each amino acid. In using either the hydrophilicity index or hydropathic index, which assigns values to each amino acid, it is preferred to conduct substitutions of amino acids where these values are ±2, with ±1 being particularly preferred, and those with in ±0.5 being the most preferred substitutions.

The variant amino acid molecule of the present invention has at least 50%, at least about 80%, or even at least about 90% but less than 100%, contiguous amino acid sequence homology or identity to the amino acid sequence of a corresponding native nucleic acid molecule or polypeptide.

The amino acid sequence of the variant fiber protein corresponds essentially to the native fiber protein's amino acid sequence. As used herein "corresponds essentially to" refers to a polypeptide sequence that will elicit a biological response substantially the same as the response generated by native fiber protein. Such a response may be at least 60% of the level generated by native fiber protein, and may even be at least 80% of the level generated by native fiber protein.

A variant of the invention may include amino acid residues not present in the corresponding native fiber protein, or may include deletions relative to the corresponding native fiber protein. A variant may also be a truncated "fragment" as compared to the corresponding native fiber protein, i.e., only a portion of a full-length protein. For, example, the polypeptide of the present invention may contain one or more of the three regions of an Ad30 fiber, i.e., a tail region (such as amino acids 1-45 of SEQ ID NO:1), a shaft region (such as amino acids 46-188 of SEQ ID NO:1) or a knob region (such as amino acids 189-371 of SEQ ID NO:1). Fiber protein variants also include peptides having at least one D-amino acid.

The variant fiber protein of the present invention may be expressed from an isolated DNA sequence encoding the variant fiber protein. The amino acid changes from the native to the variant fiber protein are achieved by changing the codons of the corresponding nucleic acid sequence. "Recombinant"

is defined as a peptide or nucleic acid produced by the processes of genetic engineering. It should be noted that it is well-known in the art that, due to the redundancy in the genetic code, individual nucleotides can be readily exchanged in a codon, and still result in an identical amino acid sequence. The terms "protein," "peptide" and "polypeptide" are used interchangeably herein.

The Ad30 fiber protein as described above may be operably linked to an amino acid sequence for a therapeutic agent. An amino acid or nucleic acid is "operably linked" when it is placed into a functional relationship with another amino acid or nucleic acid sequence. For example, DNA a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the amino acid or nucleic acid sequences being linked are contiguous, and, in the case of a secretory leader in DNA, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the term "therapeutic agent" refers to any agent or material that has a beneficial effect on the mammalian recipient. Thus, "therapeutic agent" embraces both therapeutic and prophylactic molecules having nucleic acid or protein components. The mammalian recipient may have a condition that is amenable to gene replacement therapy. As used herein, "gene replacement therapy" refers to administration to the recipient of exogenous genetic material encoding a therapeutic agent and subsequent expression of the administered genetic material in situ. Thus, the phrase "condition amenable to gene replacement therapy" embraces conditions such as genetic diseases (i.e., a disease condition that is attributable to one or more gene defects), acquired pathologies (i.e., a pathological condition that is not attributable to an inborn defect), cancers and prophylactic processes (i.e., prevention of a disease or of an undesired medical condition).

According to one embodiment, the mammalian recipient has a genetic disease and the exogenous genetic material comprises a heterologous gene encoding a therapeutic agent for treating the disease. In yet another embodiment, the mammalian recipient has an acquired pathology and the exogenous genetic material comprises a heterologous gene encoding a therapeutic agent for treating the pathology. According to another embodiment, the patient has a cancer and the exogenous genetic material comprises a heterologous gene encoding an anti-neoplastic agent. In yet another embodiment the patient has an undesired medical condition and the exogenous genetic material comprises a heterologous gene encoding a therapeutic agent for treating the condition.

The present invention also provides expression vectors containing an Ad backbone nucleic acid sequence and polynucleotide encoding a chimeric Ad fiber polypeptide comprising a tail region, a shaft region and a knob region, wherein at least one of these regions comprises an Ad30 tail region, an Ad30 shaft region or an Ad30 knob region. The expression vector may also contain a nucleotide sequence encoding a therapeutic agent.

The present invention also provides viral particles and mammalian cells containing the expression vector described above. The cell may be human, and may be from prostate, brain, breast, lung, spleen, kidney, heart, or liver. Alternatively, the cell may be a neuroprgenitor or stem cell.

The present invention also provides a method of transducing cells lacking CAR comprising contacting the cells with an expression vector or virus particle containing Ad backbone nucleic acid sequence and polynucleotide encoding a chimeric Ad fiber polypeptide comprising a tail region, a shaft region and a knob region, wherein at least one of these regions comprises an Ad30 tail region, an Ad30 shaft region or an Ad30 knob region. The cell may be a neuronal or epithelial cell, such as a human umbilical vein epithelial cell (HUVEC), or may be a tumor cell.

The present invention further provides a method of treating a genetic disease or cancer in a mammal by administering a polynucleotide, polypeptide, expression vector, or cell described above. The genetic disease or cancer may be one of the diseases listed in Tables 1-3 below.

In general, the invention relates to polypeptides that can be used as a therapeutic agent, and polynucleotides, expression vectors, virus particles and genetically engineered cells, and the use of them, for expressing the therapeutic agent. In particular, the invention may be used as a method for gene therapy that is capable of both localized and systemic delivery of a therapeutically effective dose of the therapeutic agent.

According to one aspect of the invention, a cell expression system for expressing a therapeutic agent in a mammalian recipient is provided. The expression system (also referred to herein as a "genetically modified cell") comprises a cell and an expression vector for expressing the therapeutic agent. The expression vector further includes a promoter for controlling transcription of the heterologous gene. The promoter may be an inducible promoter. The expression system is suitable for administration to the mammalian recipient. The expression system may comprises a plurality of non-immortalized genetically modified cells, each cell containing at least one recombinant gene encoding at least one therapeutic agent.

The cell expression system can be formed ex vivo or in vivo. To form the expression system ex vivo, one or more isolated cells are transduced with a virus or transfected with a nucleic acid or plasmid in vitro. The transduced or transfected cells are thereafter expanded in culture and thereafter administered to the mammalian recipient for delivery of the therapeutic agent in situ. The genetically modified cell may be an autologous cell, i.e., the cell is isolated from the mammalian recipient. The genetically modified cell(s) are administered to the recipient by, for example, implanting the cell(s) or a graft (or capsule) including a plurality of the cells into a cell-compatible site of the recipient.

According to yet another aspect of the invention, a method for treating a mammalian recipient in vivo is provided. The method includes introducing an expression vector for expressing a heterologous gene product into a cell of the patient in situ. To form the expression system in vivo, an expression vector for expressing the therapeutic agent is introduced in vivo into target location of the mammalian recipient by, for example, intraperitoneal injection.

The expression vector for expressing the heterologous gene may include an inducible promoter for controlling transcription of the heterologous gene product. Accordingly, delivery of the therapeutic agent in situ is controlled by exposing the cell in situ to conditions that induce transcription of the heterologous gene.

According to yet another embodiment, a pharmaceutical composition is disclosed. The pharmaceutical composition comprises a plurality of the above-described genetically modified cells or polypeptides and a pharmaceutically acceptable carrier. The pharmaceutical composition may be for treating a condition amenable to gene replacement therapy and the exogenous genetic material comprises a heterologous gene encoding a therapeutic agent for treating the condition. The pharmaceutical composition may contain an amount of genetically modified cells or polypeptides sufficient to deliver a therapeutically effective dose of the therapeutic agent to the patient. Exemplary conditions amenable to gene replacement therapy are described below.

According to another aspect of the invention, a method for forming the above-described pharmaceutical composition is provided. The method includes introducing an expression vector for expressing a heterologous gene product into a cell to form a genetically modified cell and placing the genetically modified cell in a pharmaceutically acceptable carrier.

According to still another aspect of the invention, a cell graft is disclosed. The graft comprises a plurality of genetically modified cells attached to a support that is suitable for implantation into the mammalian recipient. The support may be formed of a natural or synthetic material.

According to still another aspect of the invention, an encapsulated cell expression system is disclosed. The encapsulated expression system comprises a plurality of genetically modified cells contained within a capsule that is suitable for implantation into the mammalian recipient. The capsule may be formed of a natural or synthetic material.

These and other aspects of the invention as well as various advantages and utilities will be more apparent with reference to the detailed description of the invention and to the accompanying drawings.

BRIEF DESCRIPTION OF THE DRAWINGS

FIG. 1 The amino acid sequence of the Ad30 (SEQ ID NO:1) fiber is compared to the amino acid sequence of Ad5 (SEQ ID NO:5), Ad9 (SEQ ID NO:2), Ad17 (SEQ ID NO:3) and Ad3 (SEQ ID NO:4).

FIG. 2. Amino acids within Ad5 fiber that are important (in bold) or critical (in bold and underlined) for CAR binding. The amino acid sequences presented are SEQ ID NOs 13-24.

FIG. 5a. FACS analysis indicating that Ad5RSVeGFP infected 93% and 95% of A549 and HeLa cells respectively, whereas Ad5RSVeGFPf30 infected only 33% and 29% of A549 and HeLa cells respectively.

FIG. 5b. Graph depicting that after A549 and HeLa cells were incubated with Ad5:CaPi and Ad5f30:CaPi coprecipitates, Ad5 infected 95% of A549 and HeLa cells, and Ad5f30 infected 85% and 88% of A549 and HeLa cells respectively.

FIG. 7a. Graph depicting the number of eGFP positive HUVECs infected with Ad5 and Ad5f30. A two-fold increase was seen in eGFP positive cells that had been infected with Ad5f30 as compared to Ad5.

FIG. 7b. To be certain that the results shown in FIG. 7a did not indicate a difference in titer between the two viruses, both viruses were precipitated with CaPi and the virus:CaPi co-precipitant was used to infect HUVECs. The graph in FIG. 7b shows that after CaPi precipitation, over 90% of the cells were eGFP positive with either virus.

DETAILED DESCRIPTION OF THE INVENTION

Figure 3:
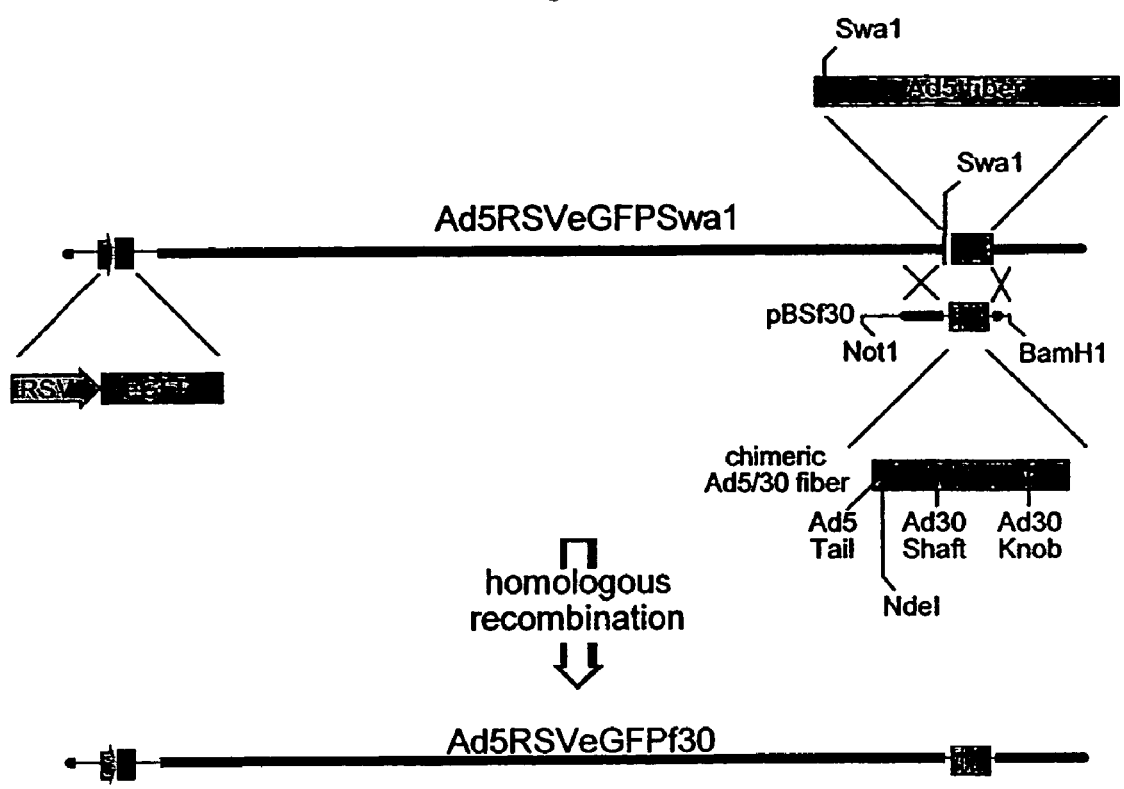
FIG. 3. Generation of chimeric virus, Ad5RSVeGFPf30. A chimeric fiber sequence was generated containing the Ad5 tail and the Ad30 shaft and knob. This chimeric fiber was then cloned into the Ad5 backbone in place of the endogenous Ad5 fiber.

Adenovirus has been shown to transduce a large number of cells including lung epithelial cells, muscle cell, endothelial cell, fibroblasts and neuronal cells. However, the efficiency is variable due to the different levels of CAR expression. Inefficient gene delivery into skeletal muscles, vascular smooth muscle, some endothelial cells and certain tumorogenic cells is a result of low expression of CAR.

Adenovirus tropism is the result of specific binding of the virus to the cell to be infected, by means of a cellular receptor. The viral C-terminal portion of fiber or "knob" is responsible for specificity of receptor recognition by the virus. Human coxsackievirus and adenovirus receptor (CAR) interacts with the fiber knob of several adenoviral serotypes (2, 4, 5, 9, 12, 15, 17, 19, 31, 41) (Bergelson, et al., (1997) Science 275: 1320-1323; Roelvink, et al., (1998) J. Virol. 72:7909-7915; Freimuth, etal., (1999) J. Virol. 73(2):1392-1398; Wang, et al., (1999) J. Virol 73(3):2559-2562; Zabner, et al., (1999) J. Virol 73(10):8689-8695), indicating that CAR is the likely cellular receptor for the serotypes mentioned. The mouse homologue of CAR (mCAR) has also been isolated and shows an ability to mediate adenoviral infection (Tomko, et al., (1997) Proc.Natl.Acad.Sci. U.S.A. 94:3352-3356; Bergelson, et al., (1997) J. Virol. 72:415-419). The majority of adenoviral serotypes have been shown to interact with CAR; however, there are some exceptions namely, Ad3 (Stevenson, et al., (1995). J. Virol. 69:2850-2857) and Ad35 (Shayakhmetov, et al., (2000) J. Virol. 74(6):2567-2583) that do not. It has been demonstrated that some D-serotype viruses utilize CAR 2. Ad30 was not among the serotypes tested.

In order to improve the utility of recombinant adenoviral vectors by increasing the therapeutic index, a capsid exhibiting a higher efficiency of transduction was sought. Such a capsid could then be used in conjunction with a gutted adenoviral genome to promote long term transgene expression with minimal immune response.

In an effort to find a capsid exhibiting a higher efficiency of transduction, numerous adenoviral serotypes were screened for infection efficiency of primary fetal rat CNS cultures and human umbilical vein epithelial cells (HUVECs) (Chillon, et al., (1999) J. Virol. 73(3):2537-2540). It was determined that Subgroup D viruses exhibit enhanced gene transfer to both culture types. It was thought that this increase in efficiency when compared to Ad5 was due to differences between the viruses in their fiber protein amino acid sequence or length. Ad30 fibers are approximately one-third shorter than those of Ad5. The importance of this difference could be attributed to the two-step process of adenoviral infection. The shorter length of the Ad30 fibers may allow higher affinity interactions with cellular $a_v$ integrins to occur. It was reasoned that such tropism could be passed to another adenovirus by replacement of its endogenous fiber sequence with that of the Ad30 fiber sequence. In order to demonstrate that the Ad30 fiber protein was responsible for the increase in CNS and HUVEC tropism, it was decided to replace the endogenous fiber sequence of Ad5 with that of Ad30. The ability of the Ad5 genome to tolerate such changes has been demonstrated by several groups (Shayakhmetov, et al., (2000) *J. Virol.* 74(6):2567-2583; Crompton, et al., (1994) *J. Gen. Virol.* 75:133-139; Gall, et al., (1996) *J. Virol.* 70:2116-2123; Gonzalez, et al., (1999) *Gene Ther.* 6(3):314-320; Krasnykh, et al., (1996) *J. Virol.* 70(10):6839-6846; Krasnykh, et al., (1998) *J. Virol.* 72:1844-1852; Legrand, et al., (1999) *J. Virol.* 73(2):907-919; Michael, et al., (1995) *Gene Ther.* 2:660-668; Miyazawa, et al., (1999) *J. Virol.* 73(7):6056-6065; Stevenson, et al., (1997) *J. Virol.* 71:4782-4790; Wickham, et al., (1995) *Gene Ther.* 2:750-756.).

Almost no information was available on Ad30 prior to the present work. There was no sequence data to be obtained and it was unknown if Ad30 like other adenoviral serotypes (2, 4, 5, 9, 12, 15, 17, 19, 31, 37?, 41) (Bergelson, et al., (1997) *Science* 275:1320-1323; Roelvink, et al., (1998) *J. Virol.* 72:7909-7915; 10 Freimuth, et al., (1999) *J. Virol.* 73(2): 1392-1398; Wang, et al., (1999) *J. Virol.* 73(3):2559-2562; Zabner, et al., (1999) *J. Virol.* 73(10):8689-8695) could bind CAR. Ad30 was propagated and viral particles were purified. Once purified particles were available, genomic DNA could be isolated and sequence data generated.

The fiber gene was sequenced using degenerate primers based on other D-serotype fiber sequences followed by specific primers as the Ad30 sequence data was generated. It was then possible to create a chimeric fiber protein consisting of Ad5 tail and Ad30 shaft/knob by overlapping PCR. This chimeric fiber protein was cloned into the Ad5 backbone replacing the endogenous Ad5 fiber by means of homologous recombination in *E coli*. A chimeric virus was thus developed that also expressed the reporter gene eGFP. Once propagated this virus was compared to normal Ad5 expressing eGFP in infection studies of cultured cells. It was found that the chimeric virus was less efficient in transduction of CAR positive cells but more efficient in transducing HUVECs.

The Ad30 Fiber Gene

To further the study of adenoviral serotypes tropic for CNS cells (Chillon, et al., (1999) *J. Virol.* 73(3):2537-2540), the Ad30 fiber gene needed to be cloned.

Ad30 genomic DNA was isolated and the fiber gene was amplified by means of degenerate primers based on known D serotype fiber sequences. As sequence data was acquired further specific primers were designed and employed until the entire nucleic acid sequence of the Ad30 fiber gene was known (SEQ ID NO:12). The amino acid sequence of Ad30 (SEQ ID NO:1) is shown in FIG. 1.

Once the sequence was available it become possible to compare its amino acid sequence with that of other sequenced fibers. Ad30 fiber is quite similar to Ad9 (SEQ ID NO:2) and Ad17 (SEQ ID NO:3), is less similar to Ad3 (SEQ ID NO:4), and is the least similar to Ad5 (SEQ ID NO:5), as shown in FIG. 1. This comparison was important in light of recent discoveries regarding the amino acid residues present in the Ad5 knob that are important for binding to CAR (Roelvink, et al., (1999) *Science* 286:1568-1571; Kirby, et al., (2000) *J. Virol.* 74(6):2804-2813).

It was found that Ad30 shares 25% overall identity of amino acid residues with Ad5 in the fiber protein. When analyzed according to regions within the fiber protein 59%, 11% and 48% identity is seen in the regions of tail, shaft and knob respectively. The 11% identity in the shaft region is due primarily to the difference in shaft length between the two fibers. Ad30 shaft is less than one-half the length of that of Ad5. Of those residues that have been shown to be critical for CAR binding two out of four are conserved in Ad30 fiber. Of those amino acid residues that have an effect on CAR binding none are conserved. These differences are illustrated in FIG. 2.

Chimeric Fiber

It was previously demonstrated that wild-type Ad30 exhibited improved tropism for vascular (endothelial) and neuronal cells, when compared to recombinant Ad5-based vectors. To show that Ad30 fiber could be responsible for this difference, a chimeric virus, Ad5RSVeGFPf30, was generated by means of homologous recombination in BJ5183 cells (Anderson, et al., (2000) *Gene Ther.* 7(12):1034-1038).

Figure 4:
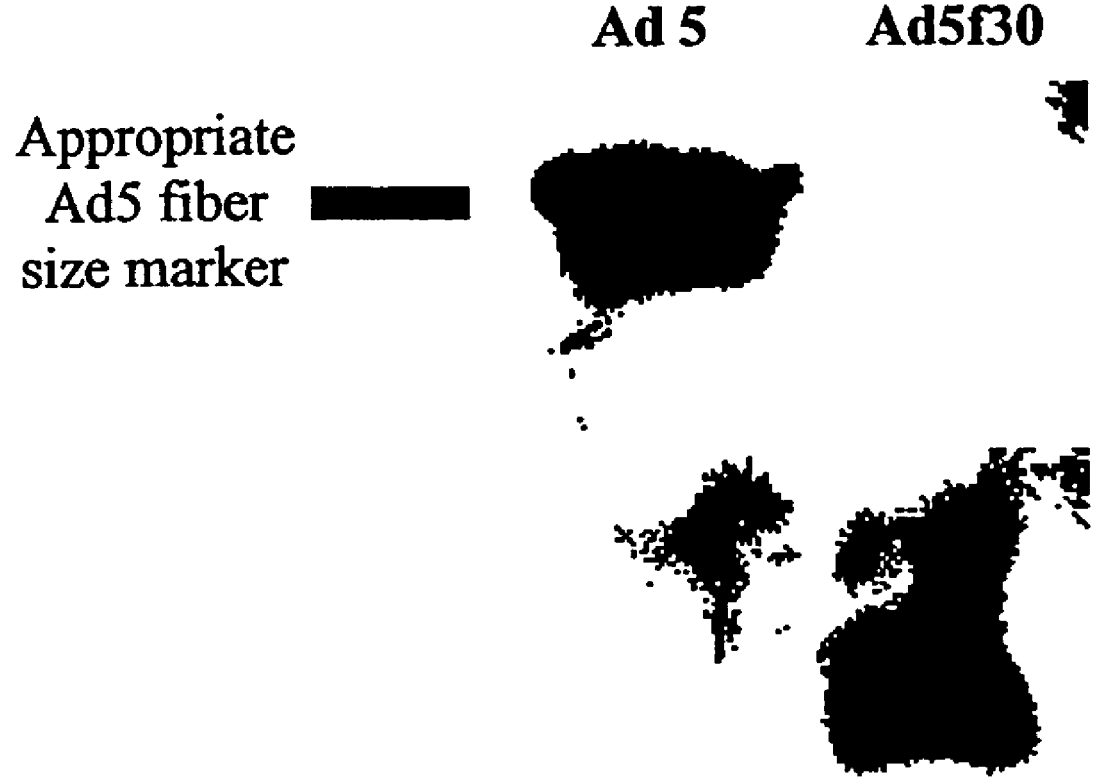
FIG. 4. Western blot analysis comparing viruses containing the endogenous Ad5 fiber to viruses containing the chimeric Ad5f30 fiber indicated that Ad5f30 indeed had a shorter fiber as compared to the endogenous fiber.

A chimeric fiber gene was created by overlapping PCR. The Ad5 tail was amplified, as were the A30 shaft and knob. These products were then combined in the second round of PCR amplification to yield a chimeric fiber gene. This gene was cloned into the Ad5 backbone in place of the endogenous Ad5 fiber as depicted in FIG. 3. The plasmid containing the chimeric Ad5f30 genome was subjected to sequence analysis to be certain that the chimeric fiber gene was correctly cloned. Western blot analysis of both viruses indicated that Ad5f30 indeed had a shorter fiber corresponding to the appropriate size (FIG. 4). This plasmid was then linearized by restriction digest and transfected into HEK293 cells to generate virus as previously described (Anderson, et al., (2000) *Gene Ther.* 7(12):1034-1038).

Ad5f30 generated CPE much slower than Ad5 (45 hrs. vs. 30 hrs.) and the total particles isolated for Ad5f30 was ~3 fold less than that for Ad5. To compare the number of infectious units of the two viruses two experiments were undertaken. First, plaque assay on HEK293 cells infected with either virus and incubated over several days was performed. Using this method the titer of Ad5f30 was 2.5' $10^9$ pfu/ml and Ad5 was 2' $10^9$ pfu/ml. To circumvent fiber-dependent titers, titers were performed with viral-CaPi co-precipitants.

To test if the delayed growth properties of Ad30 and Ad5f30 could be attributed to reduced infection efficiency, the two viruses were compared in A549 and HeLa cells. Both cell types were infected with equal particle numbers of the two viruses. It was found that Ad5 was more efficient in infecting A549 and HeLa cells than the chimeric vector, Ad5f30. A549 cells and HeLa cells were incubated in the presence of 5000 particles per cell of each virus for 1 hour at 37° C. Viral particles were then removed, the cells were washed and then incubated an additional 24 hrs. at 37° C. FACS analysis indicated that Ad5RSVeGFP infected 93% and 95% of A549 and HeLa cells respectively (FIG. 5*a*.). Ad5RSVeGFPf30 infected only 33% and 29% of A549 and HeLa cells respectively (FIG. 5*a*.).

To be certain that fiber was responsible for the differences in infection efficiencies observed and not a difference in viral particle infectivity, both adenoviral vectors were precipitated with calcium phosphate (CaPi) (Fasbender, et al., (1998) *J. Clin.Invest.* 102(1):184-193). Such precipitation of adenoviral vectors has been shown to ameliorate fiber dependent cell entry (Fasbender, et al., (1998) *J. Clin.Invest.* 102(1):184-193). After A549 and HeLa cells were incubated with Ad5: CaPi and Ad5f30:CaPi coprecipitates for 30 min at 37°, Ad5 infected 95% of A549 and HeLa cells (FIG. 5*b*.). Ad5f30 infected 85% and 88% of A549 and HeLa cells respectively (FIG. 5*b*.). These results demonstrate that the chimeric fiber of Ad5f30 is responsible for the difference in tropism initially seen between Ad5 and Ad5f30 as both viruses were shown to be nearly equal in infectivity once the requirement for the Ad5 fiber was removed. The difference in infection efficiencies without CaPi precipitation of the two viruses for A549 and HeLa cells suggested that Ad5f30 infected via a different pathway than that used by Ad5.

Figure 6:
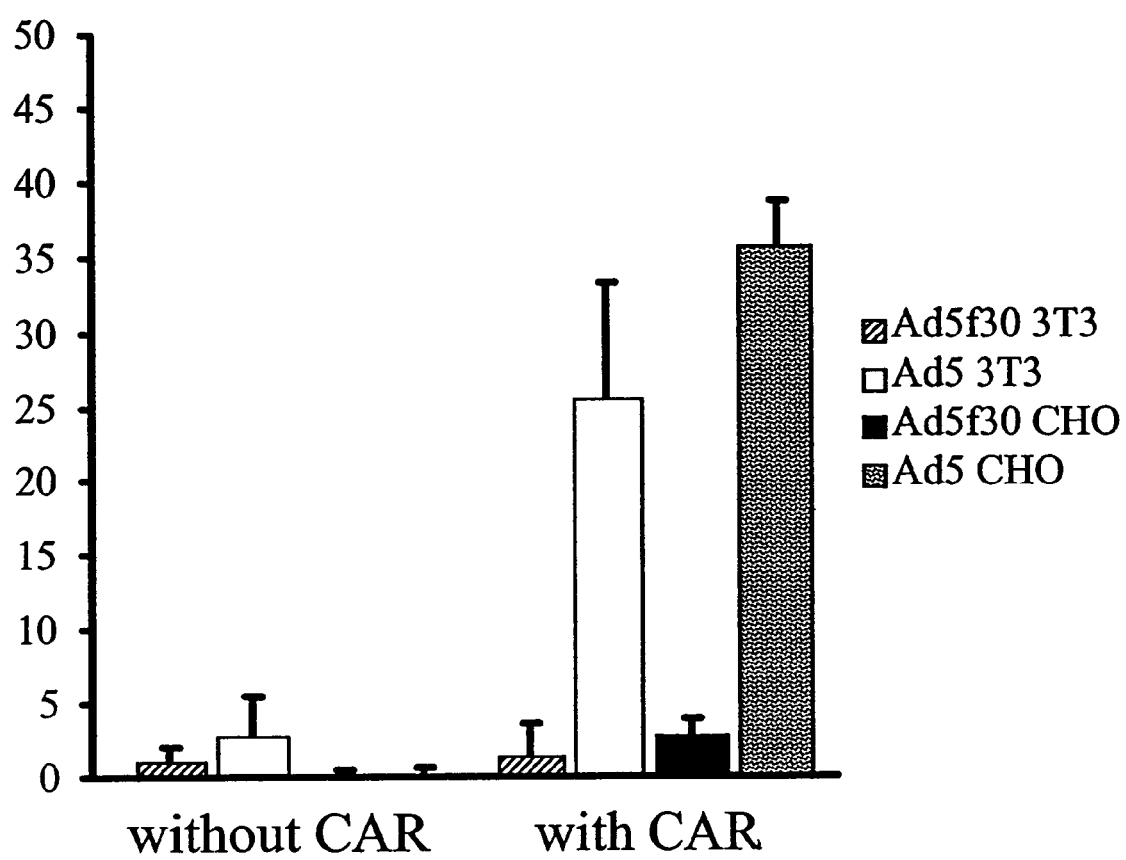
FIG. 6. Ad5 has been shown to infect cells via CAR. To assess the potential use of the CAR receptor by both viruses, 3T3 and CHO cells were used, as both cell types have been shown to express little if any CAR. The graph of FIG. 6 shows that Ad5 infected 3% and 0% of 3T3 and CHO cells respectively in the absence of CAR; Ad5f30 infected 1% of 3T3 and 0% of CHO cells in the absence of CAR. To assess infection with the addition of CAR, 3T3 cells and CHO cells were incubated with an Ad5CMVhCAR:CaPi co-precipitant for 30 min at 37° C. It was found that after such gene transfer 3T3 and CHO cells were 92% and 96% positive for CAR expression as determined by FACs. CAR expression dramatically increased Ad5 infection (21% for 3T3 and 57% for CHO cells). However, introduction of CAR had no significant impact on infection efficiency of Ad5f30 (1% and 2% for 3T3 and CHO cells).

Ad5 has been shown to infect cells via CAR (Bergelson, et al., (1997) *Science* 275:1320-1323; Roelvink, et al., (1998) *J. Virol.* 72:7909-7915; Freimuth, et al., (1999) *J. Virol.* 73(2): 1392-1398; Wang, et al., (1999) *J. Virol.* 73(3):2559-2562; Zabner, et al., (1999) *J. Virol.* 73(10):8689-8695). To assess the potential use of the CAR receptor by both viruses, 3T3 and CHO cells were used, as both cell types have been shown to express little if any CAR (Tomko, et al., (1997) *Proc.Natl.Acad.Sci.U.S.A.* 94:3352-3356; Shayakhmetov, et al., (2000) *J. Virol.* 74(6):2567-2583). Both cell types were incubated with 500 particles per cell of both viruses for 30 min. Ad5 infected 3% and 0% of 3T3 and CHO cells respectively (FIG. 6.). Ad5f30 infected 1% of 3T3 and 0% of CHO cells (FIG. 6.). To assess infection with the addition of CAR, 3T3 cells and CHO cells were incubated with an Ad5CMVhCAR: CaPi co-precipitant for 30 min at 37° C. It was found that after gene transfer 3T3 and CHO cells were 92% and 96% positive for CAR expression as determined by FACs (FIG. 6.). CAR expression dramatically increased Ad5 infection (21% for 3T3 and 57% for CHO cells). However, introduction of CAR had no significant impact on infection efficiency of Ad5f30 (1% and 2% for 3T3 and CHO cells) (FIG. 6.).

The inventors previously demonstrated that Ad30 infected of HUVECs more efficiently than Ad5 (Chillon, et al., (1999) *J. Virol.* 73(3):2537-2540). To determine if the fiber gene was responsible, confluent HUVECs were infected with Ad5 or Ad5f30 (5000 particles per cell) for one hour and quantified the number of eGFP positive cells three days later. A two-fold increase in eGFP positive cells from Ad5f30 was seen as compared to Ad5 (FIG. 7a). The results showed 72% positive cells with Ad5f30 and 36% for Ad5. A similar increase was seen with an incubation time of 15 or 30 min. To be certain that these results did not indicate a difference in titer between the two viruses, both viruses were precipitated with CaPi and the virus:CaPi co-precipitant was used to infect HUVECs. After CaPi precipitation, over 90% of the cells were eGFP positive with either virus (FIG. 7b).

Thus, the present inventors obtained, amplified and purified Ad30 wild-type particles. Genomic DNA from these particles was isolated and used to obtain the sequence of the Ad30 fiber protein by means of degenerate primers. When the Ad30 fiber sequence was compared to that of Ad5 fiber significant differences were evident. The shaft of the Ad30 fiber is less than half the length of the Ad5 fiber. Of note also, is the fact that of the seven amino acids shown to be important for CAR binding Ad30 lacks all but two. Those amino acids, conserved between Ad5 and Ad30 fibers, are in the hinge region between shaft and knob and are well conserved among most adenoviral serotypes. These results indicate that Ad30 most likely does not use CAR as its primary receptor.

Both viruses were used to infect a number of cell types. Ad5f30 was less efficient in infecting A549 and HeLa cells. A coprecipitant of Ad5f30 and CaPi, however, was very nearly equal in infection efficiency to a coprecipitant of Ad5:CaPi. These results indicated that the chimeric virus was viable and that the differences in infection efficiency were due to the different fibers present on the viral capsids. Both viruses were also tested in 3T3 and CHO cells in the presence or absence of CAR. It is evident from those experiments that the presence of CAR may not play a role in the infection efficiency of Ad5f30.

Both viruses were also tested in primary cultures. It was found that the infection efficiency of Ad5f30 was two-fold that of Ad5 at all time-points and particle concentrations when the HUVECs are confluent. As confluence of the HUVECs decreases so does the infection efficiency of Ad5f30 relative to that of Ad5. It is possible that in context of the shorter Ad30 fiber the Ad5 penton is better able to mediate viral entry. It is also possible that Ad5f30 uses another receptor present on the cell surface of the HUVEC.

It is evident from these studies that the fiber protein is responsible for the tropism and infection efficiency exhibited by a virus. Replacement of an endogenous fiber with that of a different serotype alters its infection profile. These fiber proteins are useful for various research and clinical applications.

Methods of Generating Adenoviral Vectors

Recombinant adenoviruses are useful vectors for basic research and for clinical applications. When used in delineating protein function, vectors that contain a given transgene with mutations or alterations to the coding sequence are compared at the same time. Adenoviruses can be made by standard transfection of a shuttle plasmid and viral DNA backbone into HEK 293 cells. Homologous recombination occurs in vivo, and recombinant virus can be isolated and propagated. The major drawback of this technique is that the starting viral DNA backbone, restricted of E1 containing sequences, must be 100% free of full-length Ad DNA. Otherwise, varying amounts of wild-type virus are also propagated. Alternatively, adenoviruses can be made via the streamlined method set forth in U.S. patent application Ser. No. 09/521,524 and in Anderson, et al., (2000) *Gene Ther.* 7(12):1034-1038.

Methods of Treating Genetic Disease or Cancer

The present invention provides methods of treating a genetic disease or cancer in a mammal by administering a polynucleotide, polypeptide, expression vector, viral particle or cell. For the gene therapy methods, a person having ordinary skill in the art of molecular biology and gene therapy would be able to determine, without undue experimentation, the appropriate dosages and routes of administration of the a polynucleotide, polypeptide, expression vector, viral particle or cell used in the novel methods of the present invention.

The instant invention provides a cell expression system for expressing exogenous genetic material in a mammalian recipient. The expression system, also referred to as a "genetically modified cell," comprises a cell and an expression vector for expressing the exogenous genetic material. The genetically modified cells are suitable for administration to a mammalian recipient, where they replace the endogenous cells of the recipient. Thus, the preferred genetically modified cells are non-immortalized and are non-tumorogenic.

According to one embodiment, the cells are transformed or otherwise genetically modified ex vivo. The cells are isolated from a mammal (such as a human), transformed (i.e., transduced or transfected in vitro) with a vector for expressing a heterologous (e.g., recombinant) gene encoding the therapeutic agent, and then administered to a mammalian recipient for delivery of the therapeutic agent in situ. The mammalian recipient may be a human and the cells to be modified are autologous cells, i.e., the cells are isolated from the mammalian recipient.

According to another embodiment, the cells are transformed or otherwise genetically modified in vivo. The cells from the mammalian recipient, are transformed (i.e., transduced or transfected) in vivo with a vector containing exogenous genetic material for expressing a heterologous (e.g., recombinant) gene encoding a therapeutic agent and the therapeutic agent is delivered in situ.

As used herein, "exogenous genetic material" refers to a nucleic acid or an oligonucleotide, either natural or synthetic, that is not naturally found in the cells; or if it is naturally found in the cells, it is not transcribed or expressed at biologically significant levels by the cells. Thus, "exogenous genetic material" includes, for example, a non-naturally occurring nucleic acid that can be transcribed into anti-sense RNA, as well as a "heterologous sequence" (i.e., a sequence encoding a protein that is not expressed or is expressed at biologically insignificant levels in a naturally-occurring cell of the same type). To illustrate, a synthetic or natural sequence encoding human erythropoietin (EPO) would be considered "exogenous genetic material" with respect to human peritoneal mesothelial cells since the latter cells do not naturally express EPO; similarly, a human interleukin-1 gene inserted into a peritoneal mesothelial cell would also be an exogenous gene to that cell since peritoneal mesothelial cells do not naturally express interleukin-1 at biologically significant levels. Still another example of "exogenous genetic material" is the introduction of only part of a genetic sequence to create a recombinant sequence, such as combining an inducible promoter with an endogenous coding sequence via homologous recombination.

In the certain embodiments, the mammalian recipient has a condition that is amenable to gene replacement therapy. As used herein, "gene replacement therapy" refers to administration to the recipient of exogenous genetic material encoding a therapeutic agent and subsequent expression of the administered genetic material in situ. Thus, the phrase "condition amenable to gene replacement therapy" embraces conditions such as genetic diseases (i.e., a disease condition that is attributable to one or more gene defects), acquired pathologies (i.e., a pathological condition that is not attributable to an inborn defect), cancers and prophylactic processes (i.e., prevention of a disease or of an undesired medical condition). Accordingly, as used herein, the term "therapeutic agent" refers to any agent or material that has a beneficial effect on the mammalian recipient. Thus, "therapeutic agent" embraces both therapeutic and prophylactic molecules having nucleic acid (e.g., antisense RNA) and/or protein components.

A number of diseases caused by single-gene defects have been identified (Roemer, K. and Friedmann, T., *Eur J. Biochem.* 208:211-225 (1992); Miller, A. D., *Nature* 357:455-460 (1992); Larrick, J. W. and Burck, K. L. Gene Therapy. Application of Molecular Biology, Elsevier, N.Y., (1991) and references contained therein). Examples of these diseases, and the therapeutic agents for treating the exemplary diseases, are provided in Table 1 below.

As used herein, "acquired pathology" refers to a disease or syndrome manifested by an abnormal physiological, biochemical, cellular, structural, or molecular biological state. Exemplary acquired pathologies, and the therapeutic agents for treating the exemplary pathologies, are provided in Table 2 below.

The condition amenable to gene replacement therapy alternatively can be a genetic disorder or an acquired pathology that is manifested by abnormal cell proliferation, e.g., cancers. According to this embodiment, the instant invention is useful for delivering a therapeutic agent having anti-neoplastic activity (i.e., the ability to prevent or inhibit the development, maturation or spread of abnormally growing cells), to primary or metastasized tumors, (e.g., ovarian carcinoma, mesothelioma, colon carcinoma). Therapeutic agents for treating these and other cancers include, for example, the anti-neoplastic agents provided in Table 3.

TABLE 1

Therapeutic Agents for Treating Diseases Involving Single-Gene Defects*

| Disease | Therapeutic Agent |
|---|---|
| Immunodeficiency | Adenosine deaminase |
| | Purine nucleoside phosphorylase |
| Hypercholesterolaemia | LDL receptor |
| Haemophilia A | Factor VIII |
| Haemophilia B | Factor IX |
| Gaucher's disease | Glucocerebrosidase |
| Mucopolysaccharidosis | β-glucuronidase |
| Emphysema | $\alpha_1$-antitrypsin |
| Cystic fibrosis | Cystic fibrosis trans-membrane regulator |
| Phenylketonuria | Phenylalanine hydroxylase |
| Hyperammonaemia | Ornithine transcarbamylase |
| Citrullinaemia | Arginosuccinate synthetase |
| Muscular dystrophy | Dystrophin |
| Thalassaemia | β-globin |
| Sickle cell anaemia | α-globin |
| Leukocyte adhesion deficiency | CD-18 |
| von Willebrand's disease | von Willebrand Factor |

*see Roemer, K. and Friedmann, T., Eur J. Biochem. 208: 211-225 (1992) and Miller, A. D., 1992, Nature 357: 455-460 and references contained therein

TABLE 2

Therapeutic Agents for Acquired Pathologies

Pathologies Associated with Peritoneal Dialysis

| | |
|---|---|
| Anemia | Erythropoietin |
| Peritoneal sclerosis | Fibrinolytic agents (e.g., tissue plasminogen activator (t-PA), or single chain urokinase plasminogen activator (scu-PA) |
| Peritonitis | Anti-oxidants (e.g., Superoxide Dismutase, Catalase) |
| Uremia | Urease |

Other Conditions

| | |
|---|---|
| Septic Shock | Anti-thrombotic agents (e.g., elastase-resistant form of thrombomodulin (TM)) |
| Diabetes mellitus | Insulin |
| Pituitary Dwarfism | Human growth hormone |
| Thrombosis | Hirudin, secreted form of TM |
| Post-Surgical Adhesions | Anti-thrombotic agents (e.g., thrombomodulin, hirudin), Fibrinolytic agents (e.g., TPA, scu-PA), Surfactants |
| AIDS | CD-4 |

TABLE 3

Therapeutic Agents for Treating Cancers*

| Defective Gene | Therapeutic Agent |
|---|---|
| Oncogenes | corresponding normal genes, oncogene antisense RNA, Mutated Tumor-Suppressor genes, Normal Tumor-Suppressor (e.g., p 53) |
| Unidentified defect | cytokines, the interferons, tumor necrosis factor, the interleukins. |

*see Roemer, K. and Friedmann, T., 1992, supra., and references contained therein.

Delivery of a therapeutic agent by a genetically modified cell is not limited to delivery to a particular location in the body in which the genetically modified cells would normally reside. For example, it is possible that a therapeutic agent secreted by a genetically modified cell within a coelomic cavity could reach the lymphatic network draining that coelomic cavity. Accordingly, the genetically modified cells of the invention are useful for delivering a therapeutic agent, such as an anti-neoplastic agent, to various parts of the body.

Alternatively, the condition amenable to gene replacement therapy is a prophylactic process, i.e., a process for preventing disease or an undesired medical condition. Thus, the instant invention embraces a cell expression system for delivering a therapeutic agent that has a prophylactic function (i.e., a prophylactic agent) to the mammalian recipient. Such therapeutic agents (with the disease or undesired medical condition they prevent appearing in parentheses) include: estrogen/progesterone (pregnancy); thyroxine (hypothyroidsm); and agents that stimulate, e.g., gamma-interferon, or supplement, e.g., antibodies, the immune system response (diseases associated with deficiencies of the immune system).

In summary, the term "therapeutic agent" includes, but is not limited to, the agents listed in Tables 1-3, as well as their variants or functional equivalents. As used herein, the term "functional equivalent" refers to a molecule (e.g., a peptide or protein) that has the same or an improved beneficial effect on the mammalian recipient as the therapeutic agent of which is it deemed a functional equivalent. Accordingly, the instant invention embraces therapeutic agents encoded by naturally-occurring DNAs, as well as by non-naturally-occurring DNAs that encode the same protein as encoded by the naturally-occurring DNA.

The above-disclosed therapeutic agents and conditions amenable to gene replacement therapy are merely illustrative and are not intended to limit the scope of the instant invention. The selection of a suitable therapeutic agent for treating a known condition is deemed to be within the scope of one of ordinary skill of the art without undue experimentation.

Methods for Introducing Genetic Material into Cells

The exogenous genetic material (e.g. a cDNA encoding one or more therapeutic proteins) is introduced into the cell ex vivo or in vivo by genetic transfer methods, such as transfection or transduction, to provide a genetically modified cell. Various expression vectors (i.e., vehicles for facilitating delivery of exogenous genetic material into a target cell) are known to one of ordinary skill in the art.

As used herein, "transfection of cells" refers to the acquisition by a cell of new genetic material by incorporation of added DNA. Thus, transfection refers to the insertion of nucleic acid into a cell using physical or chemical methods. Several transfection techniques are known to those of ordinary skill in the art including: calcium phosphate DNA co-precipitation (Methods in Molecular Biology, Vol. 7, Gene Transfer and Expression Protocols, Ed. E. J. Murray, Humana Press (1991)); DEAE-dextran (supra); electroporation (supra); cationic liposome-mediated transfection (supra); and tungsten particle-faciliated microparticle bombardment (Johnston, S. A., *Nature* 346:776-777 (1990)). Strontium phosphate DNA co-precipitation (Brash D. E. et al. *Molec. Cell. Biol.* 7:2031-2034 (1987) is an alternative transfection method.

In contrast, "transduction of cells" refers to the process of transferring nucleic acid into a cell using virus. A cell that has been transduced with a chimeric DNA virus (e.g., an adenovirus carrying a cDNA encoding a therapeutic agent), will not have the exogenous genetic material incorporated into its genome but will be capable of expressing the exogenous genetic material that is retained extrachromosomally within the cell.

Typically, the exogenous genetic material includes the heterologous gene (usually in the form of a cDNA comprising the exons coding for the therapeutic protein) together with a promoter to control transcription of the new gene. The promoter characteristically has a specific nucleotide sequence necessary to initiate transcription. Optionally, the exogenous genetic material further includes additional sequences (i.e., enhancers) required to obtain the desired gene transcription activity. For the purpose of this discussion an "enhancer" is simply any non-translated DNA sequence that works contiguous with the coding sequence (in cis) to change the basal transcription level dictated by the promoter. The exogenous genetic material may introduced into the cell genome immediately downstream from the promoter so that the promoter and coding sequence are operatively linked so as to permit transcription of the coding sequence. An expression vector may include an exogenous promoter element to control transcription of the inserted exogenous gene. Such exogenous promoters include both constitutive and inducible promoters.

Naturally-occurring constitutive promoters control the expression of essential cell functions. As a result, a gene under the control of a constitutive promoter is expressed under all conditions of cell growth. Exemplary constitutive promoters include the promoters for the following genes that encode certain constitutive or "housekeeping" functions: hypoxanthine phosphoribosyl transferase (HPRT), dihydrofolate reductase (DHFR) (Scharfnann et al., *Proc. Natl. Acad. Sci. USA* 88: 4626-4630 (1991)), adenosine deaminase, phosphoglycerol kinase (PGK), pyruvate kinase, phosphoglycerol mutase, the β-actin promoter (Lai et al., *Proc. Natl. Acad. Sci. USA* 86: 10006-10010 (1989)), and other constitutive promoters known to those of skill in the art. In addition, many viral promoters function constitutively in eucaryotic cells. These include the early and late promoters of SV40, the long terminal repeats (LTRs) of Moloney Leukemia Virus and other retroviruses, and the thymidine kinase promoter of Herpes Simplex Virus, among many others. Accordingly, any of the above-referenced constitutive promoters can be used to control transcription of a heterologous gene insert.

Genes that are under the control of inducible promoters are expressed only or to a greater degree, in the presence of an inducing agent, (e.g., transcription under control of the metallothionein promoter is greatly increased in presence of certain metal ions). Inducible promoters include responsive elements (REs) that stimulate transcription when their inducing factors are bound. For example, there are REs for serum factors, steroid hormones, retinoic acid and cyclic AMP. Promoters containing a particular RE can be chosen in order to obtain an inducible response and in some cases, the RE itself may be attached to a different promoter, thereby conferring inducibility to the recombinant gene. Thus, by selecting the appropriate promoter (constitutive versus inducible; strong versus weak), it is possible to control both the existence and level of expression of a therapeutic agent in the genetically modified cell. If the gene encoding the therapeutic agent is under the control of an inducible promoter, delivery of the therapeutic agent in situ is triggered by exposing the genetically modified cell in situ to conditions for permitting transcription of the therapeutic agent, e.g., by intraperitoneal injection of specific inducers of the inducible promoters that control transcription of the agent. For example, in situ expression by genetically modified cells of a therapeutic agent encoded by a gene under the control of the metallothionein promoter, is enhanced by contacting the genetically modified cells with a solution containing the appropriate (i.e., inducing) metal ions in situ.

Accordingly, the amount of therapeutic agent that is delivered in situ is regulated by controlling such factors as: (1) the nature of the promoter used to direct transcription of the inserted gene, (i.e., whether the promoter is constitutive or inducible, strong or weak); (2) the number of copies of the exogenous gene that are inserted into the cell; (3) the number of transduced/transfected cells that are administered (e.g., implanted) to the patient; (4) the size of the implant (e.g., graft or encapsulated expression system); (5) the number of implants; (6) the length of time the transduced/transfected cells or implants are left in place; and (7) the production rate of the therapeutic agent by the genetically modified cell. Selection and optimization of these factors for delivery of a therapeutically effective dose of a particular therapeutic agent is deemed to be within the scope of one of ordinary skill in the art without undue experimentation, taking into account the above-disclosed factors and the clinical profile of the patient.

In addition to at least one promoter and at least one heterologous nucleic acid encoding the therapeutic agent, the expression vector may also include a selection gene, for example, a neomycin resistance gene, for facilitating selection of cells that have been transfected or transduced with the expression vector. Alternatively, the cells are transfected with two or more expression vectors, at least one vector containing the gene(s) encoding the therapeutic agent(s), the other vector containing a selection gene. The selection of a suitable promoter, enhancer, selection gene and/or signal sequence (described below) is deemed to be within the scope of one of ordinary skill in the art without undue experimentation.

The therapeutic agent can be targeted for delivery to an extracellular, intracellular or membrane location. If it is desirable for the gene product to be secreted from the cells, the expression vector is designed to include an appropriate secretion "signal" sequence for secreting the therapeutic gene product from the cell to the extracellular milieu. If it is desirable for the gene product to be retained within the cell, this secretion signal sequence is omitted. In a similar manner, the expression vector can be constructed to include "retention" signal sequences for anchoring the therapeutic agent within the cell plasma membrane. For example, all membrane proteins have hydrophobic transmembrane regions that stop translocation of the protein in the membrane and do not allow the protein to be secreted. The construction of an expression vector including signal sequences for targeting a gene product to a particular location is deemed to be within the scope of one of ordinary skill in the art without the need for undue experimentation.

The following discussion is directed to various utilities of the instant invention. For example, the instant invention has utility as an expression system suitable for detoxifying intra- and/or extracellular toxins in situ. By attaching or omitting the appropriate signal sequence to a gene encoding a therapeutic agent capable of detoxifying a toxin, the therapeutic agent can be targeted for delivery to the extracellular milieu, to the cell plasma membrane or to an intracellular location. In one embodiment, the exogenous genetic material containing a gene encoding an intracellular detoxifying therapeutic agent, further includes sequences encoding surface receptors for facilitating transport of extracellular toxins into the cell where they can be detoxified intracellularly by the therapeutic agent. Alternatively, the cells can be genetically modified to express the detoxifying therapeutic agent anchored within the cell plasma membrane such that the active portion extends into the extracellular milieu. The active portion of the membrane-bound therapeutic agent detoxifies toxins that are present in the extracellular milieu.

In addition to the above-described therapeutic agents, some of which are targeted for intracellular retention, the instant invention also embraces agents intended for delivery to the extracellular milieu and/or agents intended to be anchored in the cell plasma membrane.

The selection and optimization of a particular expression vector for expressing a specific gene product in an isolated cell is accomplished by obtaining the coding sequence, such as with one or more appropriate control regions (e.g., promoter, insertion sequence); preparing a vector construct comprising the vector into which is inserted the coding sequence; transfecting or transducing cultured cells in vitro with the vector construct; and determining whether the gene product is present in the cultured cells.

In the present invention the adenovirus is used as an expression vector for transformation of cells. The adenovirus is frequently responsible for respiratory tract infections in humans and thus appears to have an avidity for the epithelium of the respiratory tract (Straus, S., The Adenovirus, H. S. Ginsberg, Editor, Plenum Press, New York, P. 451-496 (1984)). Moreover, the adenovirus is infective in a wide range of cell types, including, for example, muscle and endothelial cells (Larrick, J. W. and Burck, K. L., Gene Therapy. Application of Molecular Biology, Elsevier Science Publishing Co., Inc., New York, p. 71-104 (1991)). The adenovirus also has been used as an expression vector in muscle cells in vivo (Quantin, B., et al., *Proc. Natl. Acad. Sci. USA* 89:2581-2584 (1992)).

The adenovirus genome is adaptable for use as an expression vector for gene therapy, i.e., by removing the genetic information that controls production of the virus itself (Rosenfeld, M. A., et al., *Science* 252:431434 (1991)). Because the adenovirus functions in an extrachromosomal fashion, the recombinant adenovirus does not have the theoretical problem of insertional mutagenesis.

The instant invention also provides various methods for making and using the above-described genetically-modified cells. In particular, the invention provides a method for genetically modifying cell(s) of a mammalian recipient ex vivo and administering the genetically modified cells to the mammalian recipient. In one embodiment for ex vivo gene therapy, the cells are autologous cells, i.e., cells isolated from the mammalian recipient. As used herein, the term "isolated" means a cell or a plurality of cells that have been removed from their naturally-occurring in vivo location. Methods for removing cells from a patient, as well as methods for maintaining the isolated cells in culture are known to those of ordinary skill in the art.

The instant invention also provides methods for genetically modifying cells of a mammalian recipient in vivo. According to one embodiment, the method comprises introducing an expression vector for expressing a heterologous gene product into cells of the mammalian recipient in situ by, for example, injecting the vector into the recipient.

In one embodiment, the preparation of genetically modified cells contains an amount of cells sufficient to deliver a therapeutically effective dose of the therapeutic agent to the recipient in situ. The determination of a therapeutically effective dose of a specific therapeutic agent for a known condition is within the scope of one of ordinary skill in the art without the need for undue experimentation. Thus, in determining the effective dose, one of ordinary skill would consider the condition of the patient, the severity of the condition, as well as the results of clinical studies of the specific therapeutic agent being administered.

If the genetically modified cells are not already present in a pharmaceutically acceptable carrier they are placed in such a carrier prior to administration to the recipient. Such pharmaceutically acceptable carriers include, for example, isotonic saline and other buffers as appropriate to the patient and therapy.

The genetically modified cells are administered by, for example, intraperitoneal injecting or implanting the cells or a graft or capsule containing the cells in a target cell-compatible site of the recipient. As used herein, "target cell-compatible site" refers to a structure, cavity or fluid of the recipient into which the genetically modified cell(s), cell graft, or encapsulated cell expression system can be implanted, without triggering adverse physiological consequences. More than one recombinant gene can be introduced into each genetically modified cell on the same or different vectors, thereby allowing the expression of multiple therapeutic agents by a single cell.

The instant invention further embraces a cell graft. The graft comprises a plurality of the above-described genetically modified cells attached to a support that is suitable for implantation into a mammalian recipient. The support can be formed of a natural or synthetic material.

According to another aspect of the invention, an encapsulated cell expression system is provided. The encapsulated system includes a capsule suitable for implantation into a mammalian recipient and a plurality of the above-described genetically modified cells contained therein. The capsule can be formed of a synthetic or naturally-occurring material. The formulation of such capsules is known to one of ordinary skill in the art. In contrast to the cells that are directly implanted into the mammalian recipient (i.e., implanted in a manner such that the genetically modified cells are in direct physical contact with the cell-compatible site), the encapsulated cells remain isolated (i.e., not in direct physical contact with the site) following implantation. Thus, the encapsulated system is not limited to a capsule including genetically-modified non-immortalized cells, but may contain genetically modified immortalized cells.

The following examples are intended to illustrate but not limit the invention.

EXAMPLES

Example 1

Cells and Viruses

HeLa, human cervix carcinoma; American Type Culture Collection (ATCC) cells were maintained in modified Eagle medium (MEM)-10% fetal calf serum (FCS)-1% penicillin-streptomycin. A549 (ATCC) cells were maintained in RPMI 1640 medium-10% FCS-1% glutamine-penicillin-streptomycin. Human embryonic kidney-293 (HEK293) cells were maintained in DMEM-10% FCS-1% glutamine-penicillin-streptomycin, as were NIH3T3 (ATCC) cells. Chinese hamster ovary (CHO) (ATCC) cells were maintained in DMEM F12 medium supplemented with 1% penicillin-streptomycin and 10% FCS. Human umbilical vein epithelial cells (HUVEC) were harvested from umbilical chords and then maintained in M199 medium-20% FCS-1% BME vitamins-2% BME amino acids-1% glutamine-penicillin-streptomycin on plates previously coated with fibronectin (Sigma F-0895, St. Louis, Mo.). Ad30 (VR-273) was purchased from the ATCC and subsequently amplified by infection of 293 cells. Viral particles were banded in CsCl gradients, dialyzed, and stored in 100 ml aliquots at −80° C. Ad5CMVhCAR, produced by the University of Iowa Gene Transfer Vector Core, was a kind gift from Dr. Mike Welsh, University of Iowa.

Example 2

Sequencing Ad30 Fiber Protein

Viral DNA from purified Ad30 particles was isolated by standard protease treatment and ethanol precipitation methods. Degenerate primers to the 5' and 3' ends of the fiber gene were designed by means of comparison of the known sequences of four D-serotype viruses, adenovirus types 8, 9,15 and 17. They are 5'-CGGGATCCGCCACCATGT-CAAAGAGGCTCCGG-3' (AdDfiberF) (SEQ ID NO:6) and 5'-CGGGATCCTRATTCTTGGGCYATATAGG-3' (DfiberR) (SEQ ID NO:7). The fiber gene was completely sequenced in both directions (SEQ ID NO:12).

Example 3

Construction of Ad5RSVeGFPf30

The endogenous fiber sequence of Ad5 (nt 31042 to 32787) was replaced with Ad30 sequence by overlapping PCR. The Ad30 fiber was amplified such that it contained the Ad5 tail (nt 31042 to 31189, the first 147 nts.). Overlapping primers specific for the tail/shaft boundary containing 18 base-pairs of Ad5 and 18 base-pairs of Ad30 sequence were generated. In the first phase of the overlapping PCR, two DNA fragments corresponding to the Ad5 tail region (nt 1 to 147—nt 31042 to 31189) using primers 5'-CGCGGATCCGCGAT-GAAGCGCGCAAGA-3' (Ad5fiberforBamHI) (SEQ ID NO:8) and 5'-GATTGGGTCAGCCAGTTTCAAAGAGAG-TACCCCAGG-3' (17Ad5overtail) (SEQ ID NO:9) and to the Ad30 shaft and knob regions (nt 145 to 1116) using primers 5'-CCTGGGGTACTCTCTTTGAAACTGGCTGACCCA-3' (5Ad17overtail) (SEQ ID NO:10) and 5'-AAAACTAGT-TCATTCTTGGGCGATATA-3' (Ad30fRevSpel) (SEQ ID NO:11) were generated using Biolase DNA polymerase. Primers to the 5' and 3' ends were designed to incorporate restriction enzyme recognition sites, BamH1 and Spe1 respectively. After 30 PCR cycles, the Ad5 tail and Ad30 shaft/knob products were purified by agarose gel electrophoresis, mixed together and used as a template for the second phase of the overlapping PCR reaction, using Ad5forBamH1 and Ad30fRevSpel to amplify the entire chimeric 5/30 fiber. The 119-bp-long chimeric 5/30 fiber product, containing the Ad5 tail and the Ad30 shaft and knob domains, was purified by agarose gel electrophoresis, digested with Nde1 and Spe1 and ligated into a plasmid containing bases 29509-33096 of the Ad5 genome, pBS-5/30. This plasmid, linearized by Not1 and BamH 1, and pTG3602/RSV-eGFP/ Swa1 (Xia, et al., (2000) *J. Virol.* 74(23):11359-11366), linearized by Swa1 to drive homologous recombination in the region of fiber, were used to co-transform the RecA+ *E. coli* strain BJ5183. Resulting recombinants were screened by PCR and direct sequencing. Positive recombinants contained the entire Ad5 genome, flanked by Pac1 sites with the following modifications: replacement of the E1 region by the RSV-eGFP expression cassette, and replacement of the endogenous Ad5 fiber with the chimeric 5/30 fiber. This plasmid was then digested by Pac1 and transfected into HEK293 cells for the production of viral particles as previously described (Anderson, et al., (2000) *Gene Ther.* 7(12):1034-1038). CPE was evident 14 days post-transfection in 60 mm dishes of 293 cells. Lysates of Ad5RSV-eGFPf30 were used to infect a twenty plates of 293 cells. CPE was evident 40 hours post-infection. Virus was harvested and purified by standard methods as described previously. The control virus, Ad5RSV-eGFP, with non-recombinant fiber was similarly generated.

Example 4

Analysis of Recombinant Fiber

Purified Ad5RSVeGFP and Ad5RSVeGFPf30 ($2 \times 10^{10}$ particles) were boiled at 95° C. for 15 min in Laemli buffer and fractionated by SDS-PAGE. Proteins were transferred to nitrocellulose membranes, blocked with 5% skim milk in PBS-0.1% Tween for 1 hr. at RT, and incubated with a monoclonal antibody to the N-terminus of Ad5 (4D2.5 was a gift of Jeffrey Engler) (Mullis, et al., (1990) *J. Virol.* 64(11):5317-5323), diluted 1 to 2500 in PBS-0.1% Tween overnight at 4° C. The membrane was then washed 4×5 min. with PBS-0.1% Tween and incubated with peroxidase-conjugated goat anti-mouse secondary (Jackson ImmunoResearch Laboratories, Inc., West Grove, Pa.) diluted 1 to 2500 in PBS-0.1% Tween for 1 hr at RT. Membranes were washed as previously done and then developed with ECL reagent (Amersham Pharmacia) according to directions.

Example 5

Infections

To assess the infection efficiency of Ad5RSVeGFPf30 versus Ad5RSVeGFP, HeLa, A549, HUVEC, CHO and 3T3 cells were infected with both viral serotypes. HeLa and A549 cells were plated 24 hrs. previous to infection at a density of $3 \times 10^5$ cells per 60 mm dish. HUVECs were plated at a density of $1 \times 10^6$ per 60 mm dish, which had been previously coated with fibronectin 24 hrs. prior to infection. At the time of infection all media was removed from the cells and replaced with 1 ml of fresh media containing 5000 pt./cell of the virus to be tested. Cells were incubated in the presence of virus for 1 hr. at 37° C. After the virus was removed, cells were washed with fresh media and incubated an additional 24 (HeLa and A549 cells) or 72 hrs (HUVECs) at 37° C. Cells were then harvested and analyzed by fluorescence assisted cell prior to FACs analysis. CHO cells and 3T3 cells were plated and prepared in a similar manner; however, a total of 500 particles per cell was used and the cells were incubated with the virus for only 30 minutes.

Example 6

CaPi Mediated Infections

Four ml of $1 \times 10^{12}$ pts/ml Ad5RSV-eGFP or Ad5RSV-eGFPf30 were added to one ml of MEM, vortexed lightly and then precipitated by the addition of 25 ml of 1M $CaCl_2$, lightly vortexed and then incubated at RT for 20 min. Media was removed from 60 mm dishes of A549, HeLa and HUVECs, prepared as above and 1 ml of MEM containing the Ad-CaPi precipitant was added to each dish. Cells were incubated with the viral precipitant at a concentration of 500 particles/cell for 30 minutes at 37° C., washed with fresh media, and then incubated with 3 mls fresh media for an additional 24 hrs at 37° C. prior to FACs analysis.

Example 7

CAR Transfection Studies

CHO and 3T3 cells were transfected with Ad5CMVhCAR previously prepared with CaPi as described above. Twenty four hours after CAR transfection, cells were infected with 500 particles/cell of either virus for 1 half hour at 37° C. Cells were washed and incubated an additional 24 hrs. at 37° C. before FACs analysis.

Example 8

FACs Analysis

Infected cells were detached from dishes by incubation with Trypsin for 5 min at 37° C., spun down, resuspended in media with propidium iodide (PPI) added, and subjected to FACs analysis for the expression of eGFP. All analyses were performed on a Becton Dickinson flow cytometer (San Jose, Calif.) equipped with a 488-nm ion argon laser. Those cells analyzed for CAR expression were detached from dishes with EDTA, spun down and resuspended in 1% FBS/PBS at $2 \times 10^5$ cells/ml and incubated with monoclonal antibodies (mAbs) against CAR (RmcB) (Bergelson, et al., (1997) *Science* 275: 1320-1323; Hsu, et al., (1988) *J. Virol.* 62(5):1647-1652) for 45 min at 37° C. These cells were then spun down, washed and resuspended as previously with R-phycoerythrin-conjugated goat anti-mouse secondary antibodies, Jackson ImmunoResearch 115-116-146, for 45 min. at 4° C. Cells were then subjected to FACs analysis as above.

All publications, patents and patent applications are incorporated herein by reference. While in the foregoing specification this invention has been described in relation to certain embodiments, and many details have been set forth for purposes of illustration, it will be apparent to those skilled in the art that the invention is susceptible to additional embodiments and that certain of the details described herein may be varied considerably without departing from the basic principles of the invention.

REFERENCES

1. Bergelson, J. M., Cunninghame, J. A., Droguett, G., Kurt-Jones, E. A., Krithivas, A., Hong, J. S., Horwitz, M. S., Crowell, R. L. and Finberg, R. W. 1997. Isolation of a common receptor for coxsackie B viruses and adenoviruses 2 and 5. *Science* 275:1320-1323.
2. Roelvink, P. W., Lizonova, A., Lee, J. G., Li, Y., Bergelson, J. M., Finberg, R. W., Brough, D. E., Kovesdi, I. and Wickham, T. J. 1998. The coxsackivirus-adenovirus receptor protein can function as a cellular attachment protein for adenovirus serotypes from subgroups A, C, D, E, and F. *J. Virol.* 72:7909-7915.
3. Freimuth, P., Springer, K., Berard, C., Hainfeld, J., Bewley, M. and Flanagan, J. 1999. Coxsackievirus and adenovirus receptor amino-terminal immunoglobulin v-related domain binds adenovirus type 2 and fiber knob from adenovirus type 12. *J. Virol.* 73(2):1392-1398.
4. Wang, X. and Bergelson, J. M. 1999. Coxsackievirus and adenovirus receptor cytoplasmic and transmembrane domains are not essential for coxsackievirus and adenovirus infection. *J. Virol.* 73(3):2559-2562.
5. Zabner, J., Chillon, M., Grunst, T., Moninger, T. O., Davidson, B. L., Gregory, R. and Armentano, D. 1999. A chimeric type 2 adenovirus evector with a type 17 fiber enhances gene transfer to human airway epithelia. *J. Virol.* 73(10):8689-8695.
6. Tomko, R. P., Xu, R. and Philipson, L. 1997. HCAR and MCAR: The human and mouse cellular receptors for subgroup C adenoviruses and group B coxsackieviruses. *Proc. Natl. Acad. Sci. U.S.A.* 94:3352-3356.
7. Bergelson, J. M., Krithivas, A., Celi, L., Drognett, G., Horwitz, M. S., Wickham, T., Crowell, R. L. and Finberg, R. W. 1997. The murine CAR homolog is a receptor for coxsackie B viruses and adenoviruses. *J. Virol.* 72:415-419.
8. Stevenson, S. C., Rollence, M., White, B., Weaver, L. and McClelland, A. 1995. Human adenovirus serotypes 3 and 5 bind to two different cellular receptors via the fiber head domain. *J. Virol.* 69:2850-2857.
9. Shayakhmetov, D. M., Papayannopoulou, T., Stamatoyannopoulos, G. and Lieber, A. 2000. Efficient gene transfer into human CD34+ cells by a retargeted adenovirus vector. *J. Virol.* 74(6):2567-2583.
10. Chillon, M., Bosch, A., Zabner, J., Law, L., Armentano, D., Welsh, M. J. and Davidson, B. L. 1999. Group D adenoviruses infect primary central nervous system cells more efficiently than those from Group C. *J. Virol.* 73(3): 2537-2540.
11. Crompton, J., Toogood, C. I., Wallis, N. and Hay, R. T. 1994. Expression of a foreign epitope on the surface of the adenovirus hexon. *J. Gen. Virol.* 75:133-139.
12. Gall, J., Kass-Eisler, A., Leinwand, L. and Falck-Pedersen, E. 1996. Adenovirus type 5 and 7 capsid chimera: Fiber replacement alters receptor tropism without affecting primary immune neutralization epitopes. *J. Virol.* 70:2116-2123.
13. Gonzalez, R., Vereecque, R., Wickham, T. J., Vanrumbeke, M., Kovesdi, I., Bauters, F., Fenaux, P. and Quesnel, B. 1999. Increased gene transfer in acute myeloid leukemic cells by an adenovirus vector containing a modified fiber protein. *Gene Ther.* 6(3):314-320.
14. Krasnykh, V. N., Mikbeeva, G. V., Douglas, J. T. and Curiel, D. T. 1996. Generation of recombinant adenovirus vectors with modified fibers for altering viral tropism. *J. Virol.* 70(10):6839-6846.
15. Krasnykh, V., Dmitriev, I., Mikheeva, G., Miller, C. R., Belousova, N. and Curiel, D. T. 1998. Characterization of an adenovirus vector containing a heterologous peptide epitope in the HI loop of the fiber knob. *J. Virol.* 72:1844-1852.
16. Legrand, V., Spehner, D., Schlesinger, Y., Settelen, N., Pavirani, A. and Mehtali, M. 1999. Fiberless recombinant adenoviruses: virus maturation and infectivity in the absence of fiber. *J. Virol.* 73(2):907-919.
17. Michael, S. I., Hong, J. S., Curiel, D. T. and Engler, J. A. 1995. Addition of a short peptide ligand to the adenovirus fiber protein. *Gene Ther.* 2:660-668.
18. Miyazawa, N., Leopold, P. L., Hackett, N. R., Ferris, B., Worgall, S., Falck-Pedersen, E. and Crystal, R. G. 1999. Fiber swap between adenovirus subgroups B and C alters intracellular trafficking of adenovirus gene transfer vectors. *J. Virol.* 73(7):6056-6065.
19. Stevenson, S. C., Rollence, M., Marshall-Neff, J. and McClelland, A. 1997. Selective targeting of human cells by a chimeric adenovirus vector containing a modified fiber protein. *J. Virol.* 71:4782-4790.
20. Wickham, T. J., Carrion, M. E. and Kovesdi, 1. 1995. Targeting of adenovirus penton base to new receptors through replacement of its RGD motif with other receptor-specific peptide motifs. *Gene Ther.* 2:750-756.
21. Xia, H., Anderson, B., Mao, Q. and Davidson, B. L. 2000. Recombinant human adenovirus: targeting to the human transferrin receptor improves gene transfer to brain microcapillary endothelium. *J. Virol.* 74(23):11359-11366.
22. Anderson, R. D., Haskell, R. E., Xia, H., Roessler, B. J. and Davidson, B. L. 2000. A simple method for the rapid generation of recombinant adenovirus vectors. *Gene Ther.* 7(12):1034-1038.
23. Mullis, K. G., Haltiwanger, R. S., Hart, G. W., Marchase, R. B. and Engler, J. A. 1990. Relative accessibility of N-Acetylglucosamine in trimers of the adenovirus types 2 and 5 fiber proteins. *J. Virol.* 64(11):5317-5323.
24. Hsu, K. H., Lonberg-Holm, K., Alstein, B. and Crowell, R. L. 1988. A monoclonal antibody specific for the cellular receptor for the group B coxsackieviruses. *J. Virol.* 62(5): 1647-1652.
25. Roelvink, P. W., Lee, G. M., Einfeld, D. A., Kovesdi, I. and Wickham, T. J. 1999. Identification of a conserved receptor-binding site on the fiber proteins of CAR-recognizing adenoviridae. *Science* 286:1568-1571.
26. Kirby, I., Davison, E., Beavil, A. J., Soh, C. P. C., Wickham, T. J., Roelvink, P. W., Kovesdi, I., Sutton, B. J. and Santis, G. 2000. Identification of contact residues and definition of the CAR-binding site of adenovirus type 5 fiber protein. *J. Virol.* 74(6):2804-2813.
27. Fasbender, A., Lee, J. H., Walters, R. W., Moninger, T. O., Zabner, J. and Welsh, M. J. 1998. Incorporation of adenovirus in calcium phosphate precipitates enhances gene transfer to airway epithelia in vitro and in vivo. *J. Clin.Invest.* 102(1):184-193.

What is claimed is:

1. A method of transducing a cell lacking coxsackievirus and adenovirus receptor (CAR) comprising contacting the cell with an expression vector comprising an Ad backbone nucleic acid sequence and polynucleotide encoding a chimeric adenovirus (Ad) fiber polypeptide comprising at least one of the following: a tail region, a shaft region and a knob region, wherein the polynucleotide encoding a chimeric Ad fiber polypeptide encodes SEQ ID NO:1, encodes amino acids 46-188 of SEQ ID NO:1, encodes amino acids 189-371 of SEQ ID NO:1, or wherein the polynucleotide comprises SEQ ID NO:12, comprises nucleotides 1-564 of SEQ ID NO:12, comprises nucleotides 1-135 of SEQ ID NO:12, or comprises nucleotides 136-564 of SEQ ID NO:12.

2. The method of claim 1, wherein the polynucleotide encoding a chimeric Ad fiber polypeptide encodes SEQ ID NO:1.

3. The method of claim 1, wherein the shaft region comprises amino acids 46-188 of SEQ ID NO:1.

4. The method of claim 1, wherein the knob region comprises amino acids 189-371 of SEQ ID NO:1.

5. The method of claim 1, wherein the polynucleotide encoding a chimeric Ad fiber polypeptide comprises SEQ ID NO:12.

6. The method of claim 5, wherein the polynucleotide comprises nucleotides 1-564 of SEQ ID NO:12.

7. The method of claim 1, wherein the polynucleotide encoding a chimeric Ad fiber polypeptide comprises nucleotides 1-135 of SEQ ID NO:12.

8. The method of claim 1, wherein the polynucleotide comprises nucleotides 136-564 of SEQ ID NO:12.

9. The method of claim 1, wherein the tail region is an Ad5 tail region, the shaft region is an Ad30 shaft region comprising amino acids 46-188 of SEQ ID NO:1, and the knob region is an Ad30 knob region.

10. The method of claim 9, wherein the polynucleotide encoding the shaft region comprises nucleotides 136-564 of SEQ ID NO:12.

11. The method of claim 1, wherein the expression vector further comprises a nucleotide sequence encoding a therapeutic agent.

12. The method of claim 1, wherein the polynucleotide encoding a chimeric Ad fiber polypeptide is operably linked to a polynucleotide encoding an amino acid sequence for a therapeutic agent.

13. The method of claim 1, wherein the cell is a neuronal or epithelial cell.

14. The method of claim 13, wherein the cell is a human umbilical vein epithelial cell (HUVEC).

15. The method of claim 1, wherein the cell is a tumor cell.

16. The method of claim 15, wherein the tumor cell is from prostate, brain, breast, lung, spleen, kidney, heart, or liver.

17. The method of claim 1, wherein the cell is a neuroprogenitor or stem cell.

* * * * *